United States Patent
Matsuno et al.

(10) Patent No.: US 10,138,508 B2
(45) Date of Patent: Nov. 27, 2018

(54) METHOD FOR MEASURING MODIFIED NUCLEOBASE USING GUIDE PROBE, AND KIT THEREFOR

(71) Applicant: FUJIREBIO INC., Shinjuku-ku (JP)

(72) Inventors: Tatsuki Matsuno, Tokyo (JP); Mariko Horiike, Tokyo (JP)

(73) Assignee: FUJIREBIO INC., Shinjuku-ku (JP)

( * ) Notice: Subject to any disclaimer, the term of this patent is extended or adjusted under 35 U.S.C. 154(b) by 0 days.

(21) Appl. No.: 15/100,804

(22) PCT Filed: Jan. 19, 2015

(86) PCT No.: PCT/JP2015/051191
§ 371 (c)(1),
(2) Date: Jun. 1, 2016

(87) PCT Pub. No.: WO2015/108177
PCT Pub. Date: Jul. 23, 2015

(65) Prior Publication Data
US 2016/0304934 A1  Oct. 20, 2016

(30) Foreign Application Priority Data

Jan. 20, 2014 (JP) .................................. 2014-007979

(51) Int. Cl.
*C12Q 1/6804* (2018.01)
*G01N 33/53* (2006.01)

(52) U.S. Cl.
CPC ....... *C12Q 1/6804* (2013.01); *G01N 33/5308* (2013.01); *C12Q 2537/164* (2013.01); *C12Q 2563/131* (2013.01)

(58) Field of Classification Search
None
See application file for complete search history.

(56) References Cited

U.S. PATENT DOCUMENTS

| 4,208,479 | A | * | 6/1980 | Zuk | ...................... C07J 41/0016 435/7.72 |
| 2006/0286577 | A1 | * | 12/2006 | Jia | ........................ C12Q 1/6806 435/6.12 |

(Continued)

FOREIGN PATENT DOCUMENTS

| EP | 2 281 883 A1 | 2/2011 |
| EP | 2 305 807 A1 | 4/2011 |
| JP | 2012-230019 A | 11/2012 |
| WO | WO 2008/117888 | 10/2008 |

OTHER PUBLICATIONS

Extended European Search Report dated Aug. 9, 2017 in European Patent Application No. 15737483.6.

(Continued)

*Primary Examiner* — Changhwa J Cheu
(74) *Attorney, Agent, or Firm* — Oblon, McClelland, Maier & Neustadt, L.L.P.

(57) ABSTRACT

The present invention provides a method for measuring a modified nucleobase that increases detection sensitivity for the modified nucleobase in a target nucleic acid.
Specifically, the present invention provides a method for measuring a modified nucleobase including:
(1) incubating a nucleic acid sample, a capture probe, and a guide probe in a solution; and
(2) measuring the modified nucleobase using an antibody against the modified nucleobase in the solution obtained at (1).
The present invention also provides a kit for measuring a modified nucleobase including:
(I) a guide probe; and
(II) a capture probe and/or an antibody against the modified nucleobase.

11 Claims, 19 Drawing Sheets
Specification includes a Sequence Listing.

(56) References Cited

U.S. PATENT DOCUMENTS

| | | | |
|---|---|---|---|
| 2008/0124735 A1* | 5/2008 | Schuster | C12Q 1/6818 435/6.12 |
| 2010/0120033 A1 | 5/2010 | Tomigahara et al. | |
| 2011/0039273 A1 | 2/2011 | Tomigahara et al. | |
| 2011/0171647 A1 | 7/2011 | Tomigahara et al. | |
| 2012/0149593 A1* | 6/2012 | Hicks | C12Q 1/6827 506/9 |

OTHER PUBLICATIONS

William Bains, "Simplified Format for DNA Probed-Based Tests", Clinical Chemistry, XP 002772611, vol. 37 No. 2, 1991, pp. 248-253.

International Search Report dated Apr. 21, 2015 in PCT/JP2015/051191 filed on Jan. 19, 2015.

Ryoji Kurita, "DNA Methylation Analysis by Electrogenerated Chemiluminescence and Bulge-Specific Immuno-Recognition", Journal of the Society for Chemistry and Micro-Nano Systems, vol. 12, No. 1, 2013, 10 Pages (with English Abstract).

Ryoji Kurita, et al., "DNA Methylation Analysis Triggered by Bulge Specific Immuno-Recognition", Analytical Chemistry, vol. 84, No. 17, 2012, pp. 7533-7538.

Johannes Proll, et al., "Ultra-Sensitive Immunodetection of 5'Methyl Cytosine for DNA Methylation Analysis on Oligonucleotide Microarrays", DNA Research, vol. 13, 2006, pp. 37-42.

Office Action dated Oct. 2, 2018, in Japanese patent application No. 2015-557908 (with English translation) (4 pages).

* cited by examiner

Target nucleic acid (TNA)
Guide probe (GP)/Capture probe (CP)

METHOD FOR MEASURING MODIFIED NUCLEOBASE USING GUIDE PROBE, AND KIT THEREFOR

TECHNICAL FIELD

The present invention relates to a method and a kit for measuring a modified nucleobase.

BACKGROUND ART

There are a few reports about a technique that detects a modified nucleobase (e.g., methylcytosine and hydroxyl methylcytosine) in a target nucleic acid, especially a technique that detects it by immunoassays (Patent Literature 1 and Non-Patent Literature 1 and 2).

PRIOR ART REFERENCE

Patent Literature

Patent Literature 1: Japanese Patent Application Laid-open No. 2012-230019

Non-Patent Literature

Non-Patent Literature 1: Proll et al., DNA Research, 13, 37-42 (2006)
Non-Patent Literature 2: Kurita et al., Anal. Chem., 2012, 84, 7533-7538

SUMMARY OF INVENTION

Problem to be Solved by the Invention

There is a demand for improving detection sensitivity for a modified nucleobase in a target nucleic acid.

The inventors of the present invention, through an investigation of a measurement system for the modified nucleobase in the target nucleic acid, have revealed that there is a problem (Specific Problem I) in that detection sensitivity for a modified nucleobase in a double-stranded target nucleic acid is lower (about 1/10) than that for a modified nucleobase in a single-stranded target nucleic acid (Reference Example 1). This is because it is considered that a complementary strand and a capture probe compete against each other for the target nucleic acid containing the modified nucleobase and that hybrid formation efficiency between the target nucleic acid and the capture probe (efficiency of capturing the target nucleic acid to a solid phase) is low (FIG. 2).

In a conventional method for measuring the modified nucleobase in the target nucleic acid using the capture probe, a hybrid including the target nucleic acid and the capture probe is formed (FIG. 3). The conventional method has a potential problem (Specific Problem II) in that a non-hybridized region (a single-stranded region) of the target nucleic acid in this hybrid forms a secondary structure, whereby the modified nucleobase contained in this secondary structure is difficult to be measured (in other words, detection sensitivity is low) (FIG. 3).

An object of the present invention is to increase detection sensitivity for a modified nucleobase in a target nucleic acid.

Another object of the present invention is to increase detection sensitivity for a modified nucleobase in a double-stranded target nucleic acid (that is, to solve Specific Problem I).

Still another object of the present invention is to increase detection sensitivity for a modified nucleobase by avoiding the formation of the secondary structure (that is, to solve Specific Problem II).

Still another object of the present invention is to develop a methodology that can solve these specific problems simultaneously.

Means for Solving Problem

As a result of intensive investigations, the inventors of the present invention have found out that in the measurement of the modified nucleobase in the target nucleic acid, the problems can be solved by using a guide probe (FIG. 1). The inventors of the present invention also have found out that using the guide probe in the presence of a nucleic acid denaturant can solve the problems more finely and have achieved the present invention.

Accordingly, the present invention is as follows:

[1] A method for measuring a modified nucleobase, the method comprising:
 (1) incubating a nucleic acid sample, a capture probe, and a guide probe in a solution; and
 (2) measuring the modified nucleobase using an antibody against the modified nucleobase in the solution obtained at (1).
[2] The method according to [1], wherein the nucleic acid sample contains a target nucleic acid containing the modified nucleobase, and the steps (1) and (2) are performed by (1') and (2'), respectively:
 (1') reacting the nucleic acid sample containing the target nucleic acid containing the modified nucleobase, the capture probe, and the guide probe in a solution by incubation to form a hybrid including the target nucleic acid, the capture probe, and the guide probe; and
 (2') measuring the modified nucleobase using the antibody against the modified nucleobase in the solution containing the hybrid.
[3] The method according to [1] or [2], further comprising combining the nucleic acid sample with the capture probe and the guide probe in a solution to prepare a solution containing the nucleic acid sample, the capture probe, and the guide probe.
[4] The method according to any one of [1] to [3], wherein the nucleic acid sample is a sample containing a single-stranded target nucleic acid containing the modified nucleobase.
[5] The method according to any one of [1] to [3], wherein the nucleic acid sample is a sample containing a double-stranded target nucleic acid containing the modified nucleobase.
[6] The method according to any one of [1] to [5], wherein the nucleic acid sample is a sample containing a target DNA containing the modified nucleobase.
[7] The method according to any one of [1] to [6], comprising incubating the nucleic acid sample, the capture probe, and the guide probe in a solution in the presence of a nucleic acid denaturant.
[8] The method according to any one of [1] to [7], comprising incubating the nucleic acid sample, the capture probe, and the guide probe in a solution in the presence of both the nucleic acid denaturant and a surfactant.
[9] The method according to any one of claims [1] to [8], wherein the capture probe is a heterogeneous nucleic acid probe.

[10] The method according to any one of claims [1] to [9], wherein the guide probe is a homogeneous nucleic acid probe.

[11] The method according to any one of claims [1] to [10], wherein a nucleobase composing the modified nucleobase is cytosine.

[12] The method according to any one of claims [1] to [11], wherein the modified nucleobase is methylcytosine.

[13] A kit for measuring a modified nucleobase, the kit comprising:
(I) a guide probe; and
(II) a capture probe and/or an antibody against the modified nucleobase.

[14] The kit according to [13], further comprising a nucleic acid denaturant.

[15] The kit according to [14], further comprising a surfactant.

Effect of the Invention

The present invention can increase detection sensitivity for a modified nucleobase in a target nucleic acid by using a guide probe.

The present invention can also increase detection sensitivity for a modified nucleobase in a double-stranded target nucleic acid by using the guide probe or, as needed, by using the guide probe in the presence of a nucleic acid denaturant.

Furthermore, the present invention can increase detection sensitivity for a modified nucleobase by avoiding the formation of the secondary structure by using the guide probe.

Furthermore, the present invention can reduce a background value of a detection signal by using the guide probe in the presence of both the nucleic acid denaturant and a surfactant.

BRIEF DESCRIPTION OF DRAWINGS

R-N: Nucleotide residue having a modified nucleobase
N: Nucleotide residue having a non-modified nucleobase, which composes target nucleic acid N': Nucleotide residue composing a guide probe or a capture probe N1 or N2 or both N1 and N2 may have substituent R.)
R: Substituent that nucleobase has

EMBODIMENTS FOR CARRYING OUT THE INVENTION

Figure 1:
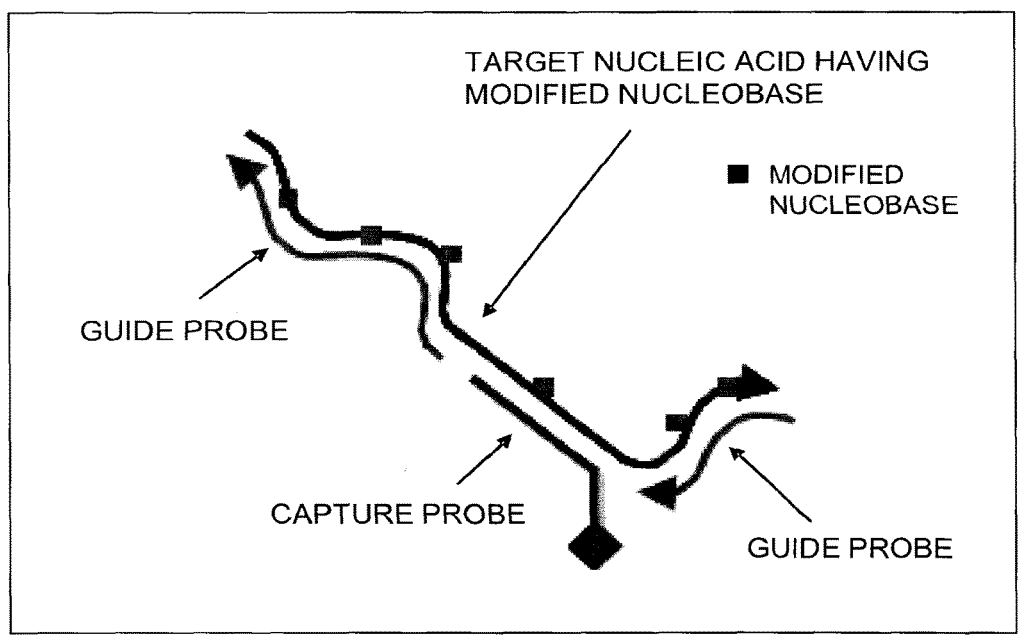
FIG. 1 is a diagram of an overview of a method of the present invention.
Figure 2:
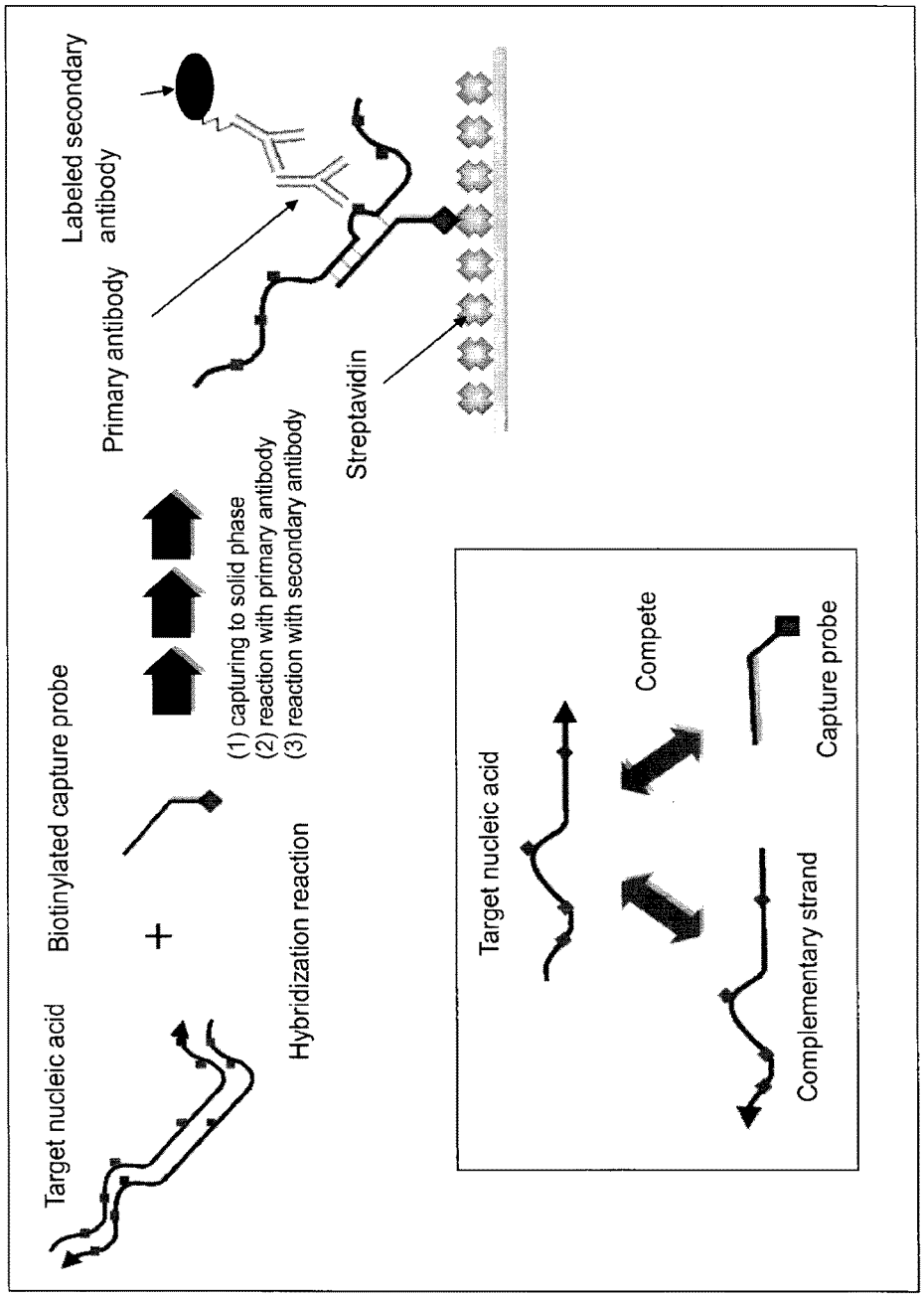
FIG. 2 is a diagram of an overview of a problem (Specific Problem I) related to the measurement of a modified nucleobase. Detection sensitivity for a modified nucleobase in a double-stranded target nucleic acid is lower than that for a modified nucleobase in a single-stranded target nucleic acid. This is because it is considered that a complementary strand and a capture probe compete against each other for the target nucleic acid containing the modified nucleobase and that hybrid formation efficiency between the target nucleic acid and the capture probe (efficiency of capturing the target nucleic acid to a solid phase) is low.

The present invention provides a method for measuring a modified nucleobase. The present invention includes:
(1) incubating a nucleic acid sample, a capture probe, and a guide probe in a solution; and
(2) measuring a modified nucleobase using an antibody against the modified nucleobase in the solution obtained at (1).

The nucleic acid sample is a sample containing a target nucleic acid containing a modified nucleobase or a sample suspected to contain the target nucleic acid. The nucleic acid sample may also be a biological sample collected from an organism, an environmental sample, or the like. Examples of the organism from which the biological sample is derived include animals such as mammals (e.g., humans, monkeys, mice, rats, rabbits, cattle, pigs, horses, goats, and sheep) and birds (e.g., chickens), insects, microorganisms, plants, fungi, and fishes. The biological sample may also be a blood-related sample that is blood itself or a blood-derived sample (e.g., whole blood, blood serum, or blood plasma), saliva, urine, milk, tissue or cell extract, or a mixture thereof. The biological sample may further be derived from mammals contracting diseases (e.g., cancer and leukemia) or mammals that may contract diseases. Examples of the environmental sample include samples derived from soil, sea water, and fresh water that may contain nucleic acids. These samples may be subjected to another treatment before being used in the method of the present invention. Examples of the treatment include extraction and fragmentation (e.g., treatment with an enzyme such as a restriction enzyme) of nucleic acids (e.g., DNA such as genomic DNA and RNA) and dissociation of strands of nucleic acids (e.g., dissociation of a double-stranded nucleic acid through heat treatment). Consequently, the method of the present invention may further include extracting a nucleic acid from the nucleic acid sample, and/or fragmenting the nucleic acid, and/or dissociating the strands of the nucleic acid. The method of the present invention may also further include treating the sample by centrifugation, extraction, filtration, precipitation, heating, freezing, refrigeration, stirring, or the like.

The target nucleic acid is any natural nucleic acid or artificial nucleic acid, preferably DNA or RNA as natural nucleic acids, and more preferably DNA. The target nucleic acid is also a coding region or a non-coding region (e.g., a transcriptional regulation region) of DNA. The number of nucleotide residues composing the target nucleic acid (that is, the length of the target nucleic acid) is not limited to a particular number so long as it enables hybridization with the capture probe and the guide probe and may be 20 or more, 25 or more, 30 or more, 35 or more, 40 or more, 45 or more, or 50 or more, for example. The number of nucleotides composing the target nucleic acid may also be any number that may occur by fragmentation of genomic DNA, for example. The number of the nucleotides composing the target nucleic acid may be 10,000 or less, 5,000 or less, 2,000 or less, 1,000 or less, 500 or less, 300 or less, 200 or less, 150 or less, or 100 or less, for example. A GC content of the target nucleic acid is not limited to a particular value and may be 10% or more, 20% or more, 30% or more, 40% or more, 50% or more, or 60% or more, for example. The GC content of the target nucleic acid may also be 90% or less, 80% or less, or 70% or less, for example. The number of modified nucleobases that the target nucleic acid contains or may contain is not limited to a particular number so long as it is one or more (e.g., 1 to 100, 1 to 50, 1 to 30, 1 to 20, 1 to 10, or 1 to 5).

In the present invention, the modified nucleobase refers to a nucleobase having a structure in which a normal nucleobase selected from the group consisting of adenine (A), guanine (G), cytosine (C), thymine (T), and uracil (U) is modified. When the target nucleic acid is DNA, examples of the term "nucleobase" in the expression "modified nucleobase" include adenine (A), guanine (G), cytosine (C), and thymine (T). When the target nucleic acid is RNA, examples thereof include adenine (A), guanine (G), cytosine (C), and uracil (U). The nucleobase is preferably cytosine (C). Examples of modification include introduction of a substituent to the normal nucleobase, elimination of a group (e.g., an amino group, an oxo group, and a methyl group) that the normal nucleobase has, and exchange of the group that the normal nucleobase has with a substituent. The substituent is not limited to a particular type so long as it is one that naturally occurring nucleobases can have, and examples thereof include the substituents that the modified nucleobases in the modified nucleotides described in Administrative Instructions under the Patent Cooperation Treaty (the version enforced on Jan. 1, 2009), Annex C, Appendix 2, Table 2: List of Modified Nucleotides have. The modified nucleotides described in the literature can be the same as the modified nucleotides described in "Guidelines for Preparation of Specifications Containing Base Sequences or Amino Acid Sequences (July of 2002) or (December of 2009)," Annex 2, Table 2: Modified Base Table disclosed by the Japan Patent Office. Consequently, concerning the modified nucleobase, the guidelines can also be referred to. The substituent is preferably methyl, hydroxymethyl, or carboxyl and more preferably methyl or hydroxymethyl. The position of the modification such as substitution is not limited to a particular position and is at least one of the 2-position or the 4- to 6-positions, for example, and preferably the 5-position for the nucleobase (C, T, or U) having a pyrimidine ring and is at least one of the 2-position, the 6-position, or the 8-position, for example, for the nucleobase (A or G) having a purine ring.

The modified nucleobase is not limited to a particular type so long as it can naturally occur, and examples thereof include the modified nucleobases that the modified nucleotides described in Administrative Instructions under the Patent Cooperation Treaty (the version enforced on Jan. 1, 2009), Annex C, Appendix 2, Table 2: List of Modified Nucleotides have. The modified nucleotides described in the literature can be the same as the modified nucleotides described in the guidelines, Annex 2, Table 2: Modified Base Table. Consequently, concerning the modified nucleobase, the guidelines can also be referred to. The modified nucleobase is preferably methylcytosine (e.g., 5-methylcytosine), hydroxymethylcytosine (e.g., 5-hydroxymethylcytosine), or carboxylcytosine (e.g., 5-carboxylcytosine). The modified nucleobase is more preferably methylcytosine (e.g., 5-methylcytosine) or hydroxymethylcytosine (e.g., 5-hydroxymethylcytosine). It is known that the modified nucleobase brings about changes in functions of nucleic acids (e.g., a change in the transcriptional regulation capability of a certain gene).

The capture probe used in the present invention is a first nucleic acid molecule having the capability of hybridizing with the target nucleic acid and can be immobilized to a solid phase. In the present invention, the capture probe is designed so as not to hybridize with the guide probe.

The capture probe can include nucleic acids homogeneous and/or heterogeneous with respect to the target nucleic acid. The term "homogeneous" means that the capture probe has the same backbone structure as a backbone structure (a structure including a sugar moiety and a phosphoric acid moiety) of the target nucleic acid as the whole of the backbone structure. The term "heterogeneous" means that the capture probe has a backbone structure different from the backbone structure (the structure including the sugar moiety and the phosphoric acid moiety) of the target nucleic acid as part or the whole of the backbone structure. Consequently, the type of the capture probe may be determined in accordance with the type of the target nucleic acid. When the target nucleic acid is DNA, for example, a DNA probe can be used as the capture probe of the homogeneous nucleic acid, and a nucleic acid probe other than the DNA probe can be used as the capture probe of the heterogeneous nucleic acid. When the target nucleic acid is natural RNA, a normal RNA probe including RNA homogeneous with the natural RNA can be used as the capture probe of the homogeneous nucleic acid, and a nucleic acid probe other than the normal RNA probe can be used as the capture probe of the heterogeneous nucleic acid. The capture probe may preferably include the nucleic acid heterogeneous with respect to the target nucleic acid.

Examples of the capture probe include DNA probes, RNA probes, peptide nucleic acid (PNA) probes, locked nucleic acid (LNA, or also called bridged nucleic acid (BNA)) probes, phosphorothioate (S-oligo) nucleic acid probes, and chimera nucleic acid probes in which two or more such nucleic acid probes are coupled and/or mixed with each other (the chimera nucleic acid probe inevitably contains a nucleic acid heterogeneous with respect to the target nucleic acid). Examples of the RNA probes include a normal RNA probe including a natural ribonucleotide having a hydroxyl group at the 2'-position and a modified RNA probe including a ribonucleotide the 2'-position hydroxyl group or other group of which is modified. The modified RNA probe may be a ribonuclease-resistant RNA probe. Examples of the modified RNA probe include a 2'-O-alkylated RNA probe.

The 2'-O-alkylated RNA probe is preferably 2'-O—$C_{1\text{-}6}$alkylated RNA probe. The $C_{1\text{-}6}$ alkyl group of the $C_{1\text{-}6}$ alkylation is a linear, branched, or cyclic $C_{1\text{-}6}$ alkyl group, and examples thereof include a methyl group, an ethyl group, a propyl group (e.g., n-propyl and iso-propyl), a butyl group (e.g., n-butyl, iso-butyl, sec-butyl, and tert-butyl), a pentyl group, and a hexyl group. In terms of easiness of manufacture and acquisition or the like, the 2'-O—$C_{1\text{-}6}$ alkylated RNA probe is preferably a 2'-O-methylated RNA probe.

The number of nucleotide residues contained in the capture probe (that is, the length of the capture probe) is not limited to a particular number so long as the length is enough to enable hybridization with the target nucleic acid, and the number may be 12 or more, preferably 15 or more, preferably 18 or more, and more preferably 20 or more, for example. The number of nucleotides composing the capture probe may also be 100 or less, 80 or less, 60 or less, or 50 or less, for example. A GC content in a region that can hybridize with the target nucleic acid in the capture probe may be 10% or more, 20% or more, 30% or more, 40% or more, 50% or more, or 60% or more, for example. The GC content in this region may also be 90% or less, 80% or less, or 70% or less, for example. The capture probe can be prepared by a method of synthesizing a probe known in the relevant field, for example.

The capture probe is used in the form of being free or the form of being immobilized to the solid phase at Step (1). Consequently, the capture probe may be labeled with a substance or a group that enables immobilization to the solid phase. The labeling can be performed either at the 5'-end or the 3'-end of the capture probe, for example. Examples of the substance or group that enables immobilization to the solid phase include groups or substances that enable covalent binding to the solid phase and affinity substances. Examples of the substances or groups that enable covalent binding to the solid phase include a thiol group or substances having a thiol group (the thiol group introduced into the capture probe can bind to a maleimide group on the solid phase) and an amino group or substances having an amino group (the amino group introduced into the capture probe can bind to maleic anhydride on the solid phase). Examples of the affinity substances include streptavidin, biotin, digoxigenin, dinitrophenol, fluorescein, and fluorescein isothiocyanate. In this case, the solid phase coated with another affinity substance having affinity with the affinity substance that the capture probe has can be used. When being used in the form of being free at step (1), the capture probe may be immobilized to the solid phase after formation of a hybrid.

The guide probe is a second nucleic acid molecule having the capability of hybridizing with the target nucleic acid. The guide probe can hybridize with the target nucleic acid in a second region different from a first region in the target nucleic acid with which the capture probe hybridizes. The guide probe is designed so as not to hybridize with the capture probe. The guide probe may be a complementary strand with respect to part of the target nucleic acid. One or a plurality of (e.g., two, three, four, or five) guide probes can be used with respect to one target nucleic acid. The guide probes can be designed so as to hybridize with different regions within the one target nucleic acid, for example.

The guide probe can include nucleic acids homogeneous or heterogeneous with respect to the target nucleic acid. The term "homogeneous" means that the guide probe has the same backbone structure as the backbone structure (the structure including the sugar moiety and the phosphoric acid moiety) of the target nucleic acid. The term "heterogeneous"

means that the guide probe has a backbone structure different from the backbone structure (the structure including the sugar moiety and the phosphoric acid moiety) of the target nucleic acid. Consequently, the type of the guide probe may be determined in accordance with the type of the target nucleic acid. When the target nucleic acid is DNA, for example, a DNA probe can be used as the guide probe of the homogeneous nucleic acid, and a nucleic acid probe other than the DNA probe can be used as the guide probe of the heterogeneous nucleic acid. When the target nucleic acid is natural RNA, a normal RNA probe including RNA homogeneous with the natural RNA can be used as the guide probe of the homogeneous nucleic acid, and a nucleic acid probe other than the normal RNA probe can be used as the guide probe of the heterogeneous nucleic acid. The guide probe may preferably include the nucleic acid homogeneous with respect to the target nucleic acid.

Examples of the guide probe include DNA probes, RNA probes, peptide nucleic acid (PNA) probes, locked nucleic acid (LNA, also called bridged nucleic acid (BNA)) probes, phosphorothioate (S-oligo) nucleic acid probes, and chimera nucleic acid probes in which two or more such nucleic acid probes are coupled and/or mixed with each other. Examples of the RNA probe include probes similar to those described above with respect to the capture probe.

The number of nucleotide residues composing the guide probe (that is, the length of the guide probe) is not limited to a particular number so long as the length is enough to enable hybridization with the target nucleic acid, and the number may be 12 or more, preferably 15 or more, preferably 18 or more, and more preferably 20 or more, for example. The number of nucleotides composing the guide probe may also be 200 or less, 150 or less, 120 or less, or 100 or less, for example. A GC content in a region that can hybridize with the target nucleic acid in the guide probe may be 10% or more, 20% or more, 30% or more, 40% or more, 50% or more, or 60% or more, for example. The GC content in this region may also be 90% or less, 80% or less, or 70% or less, for example. The guide probe can be prepared by a method of synthesizing a probe known in the relevant field, for example.

At step (1), the incubation is performed in an appropriate solution on the condition that, when the target nucleic acid is contained in the nucleic acid sample, a hybridization reaction of the capture probe (being free or immobilized to the solid phase described below), the guide probe (being free), and the target nucleic acid in the nucleic acid sample is made possible. As the solution, a buffer solution (e.g., a Tris buffer solution) can be used, for example. Hybridization conditions, which vary depending on the number of nucleotides involved in the hybridization (that is, the lengths of the target nucleic acid, the capture probe, and the guide probe) and the like, are 2 minutes to 24 hours (preferably 10 minutes to 120 minutes) at 25° C. to 80° C. (preferably 37° C. to 70° C.), for example. The incubation may be performed in the solid phase or in the presence of the solid phase to which the capture probe can be immobilized. Alternatively, a solution obtained after the incubation may be caused to coexist with the solid phase.

The expression "incubating a nucleic acid sample, a capture probe, and a guide probe in a solution" at step (1) intends to incubate the nucleic acid sample, the capture probe, and the guide probe simultaneously or with a time difference so that the hybrid including the target nucleic acid (when the nucleic acid sample contains the target nucleic acid), the capture probe, and the guide probe will finally be formed.

Consequently, the expression specifically contains the following modes:

(1-1) incubating the nucleic acid sample, the capture probe, and the guide probe in the solution simultaneously;

(1-2) incubating the nucleic acid sample and the capture probe first (when the nucleic acid sample contains the target nucleic acid, an intermediate hybrid including the target nucleic acid and the capture probe is formed), combining the solution obtained by the incubation with the guide probe, and further incubating the solution (when the nucleic acid sample contains the target nucleic acid, a hybrid including the target nucleic acid, the capture probe, and the guide probe is formed); and (1-3) incubating the capture probe and the guide probe first (an intermediate hybrid including the capture probe and the guide probe is formed), combining the solution obtained by the incubation with the nucleic acid sample, and further incubating the solution (when the nucleic acid sample contains the target nucleic acid, a hybrid including the target nucleic acid, the capture probe, and the guide probe is formed).

When the nucleic acid sample does not contain the target nucleic acid, even by incubating the nucleic acid sample, the capture probe and the guide probe in the solution, the aimed hybrid including the target nucleic acid, the capture probe, and the guide probe is not formed. In this case, the modified nucleobase cannot be detected at step (2) described below, but it can be determined that the modified nucleobase is not present in the nucleic acid sample.

When the nucleic acid sample contains the target nucleic acid not containing the modified nucleobase (in other words, the target nucleic acid containing non-modified nucleobases alone), by incubating the nucleic acid sample, the capture probe, and the guide probe in the solution, the target nucleic acid not containing the modified nucleobase, the capture probe, and the guide probe react (meaning the hybridization reaction, the same hereinafter) with each other, whereby a hybrid including the target nucleic acid, the capture probe, and the guide probe is formed. In this case, the modified nucleobase cannot be detected at step (2) described below, but it can be determined that the modified nucleobase is not present in the nucleic acid sample (even though the target nucleic acid is present) or, in other words, that a certain nucleobase in the target nucleic acid is not modified.

When the nucleic acid sample contains the target nucleic acid containing the modified nucleobase, by incubating the nucleic acid sample, the capture probe, and the guide probe in the solution, the target nucleic acid containing the modified nucleobase, the capture probe, and the guide probe react with each other, whereby a hybrid including the target nucleic acid, the capture probe, and the guide probe is formed. In this case, it can be determined that the modified nucleobase is present at step (2) described below, and the modified nucleobase can also be quantified.

In the present invention, the hybrid is a hybridization complex including the target nucleic acid, the capture probe, and the guide probe having a double-stranded structure of the target nucleic acid and the capture probe formed by the hybridization between the target nucleic acid and the capture probe and a double-stranded structure of the target nucleic acid and the guide probe formed by the hybridization between the target nucleic acid and the guide probe.

In the hybrid, the number of nucleotide residues of the target nucleic acid and the capture probe corresponding to a double-stranded structure part of the target nucleic acid and the capture probe and the number of nucleotide residues of the target nucleic acid and the guide probe corresponding to a double-stranded structure part of the target nucleic acid and the guide probe (that is, the lengths of the double-stranded structure parts) are not limited to a particular number so long as the lengths are enough to enable hybridization with the target nucleic acid, and the number of the nucleotide residues may be 10 or more, preferably 12 or more, more preferably 15 or more, further more preferably 18 or more, and particularly preferably 20 or more, for example. The number of the nucleotide residues may also be 200 or less, 150 or less, 120 or less, 100 or less, 80 or less, 50 or less, or 30 or less, for example. A melting temperature (Tm1) between the target nucleic acid and the capture probe and a melting temperature (Tm2) between the target nucleic acid and the guide probe can be adjusted appropriately in accordance with the lengths of the capture probe and the guide probe (that is, the number of the nucleotide residues). The capture probe and the guide probe may be designed so that the temperature difference between Tm1 and Tm2 will be within the range of 20° C., 15° C., 10° C., or 5° C., for example.

In an embodiment, each of the probes (the guide probe and the capture probe) may be designed so that an unpaired part of the modified nucleobase will be formed in the (a) the double-stranded structure part including the target nucleic acid and the guide probe in the hybrid and/or (b) the double-stranded structure part including the target nucleic acid and the capture probe in the hybrid. The unpaired part of the modified nucleobase can be introduced to facilitate detection of the modified nucleobase by an antibody. To form the unpaired part, probes (the guide probe and the capture probe) each having a nucleotide sequence that is not perfectly complementary with respect to the target nucleic acid in the double-stranded structure part may be used, for example.

Figure 17A:
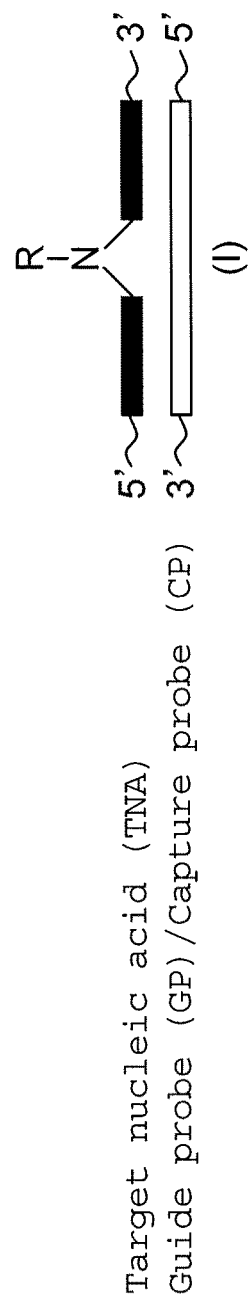
FIGS. 17A-17C show formations of unpaired part of modified nucleobase in double-stranded structure part including target nucleic acid and guide probe or capture probe in hybrid (1).
Figure 17B:
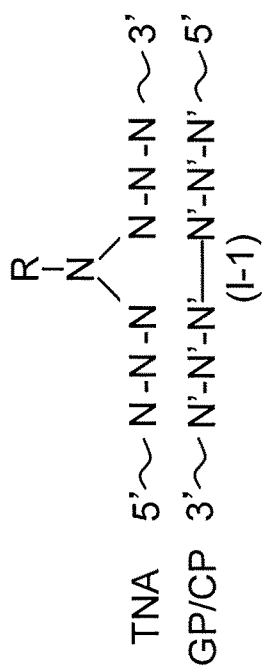
Figure 17C:
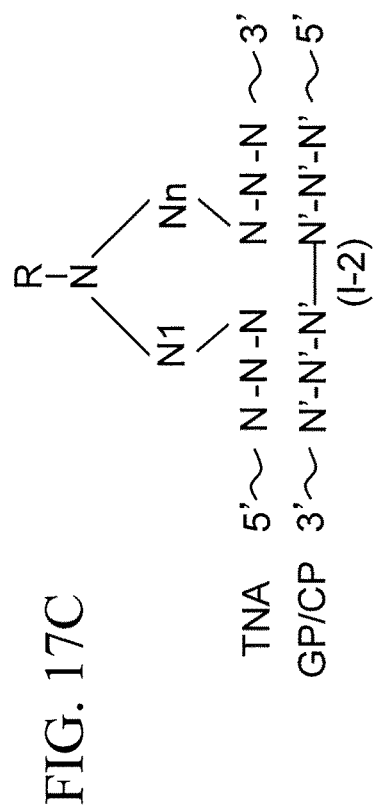

An example of the probe in which the unpaired part of the modified nucleobase is formed in the (a) and (b) double-stranded structure parts is a probe lacking a nucleotide residue complementary with respect to a nucleotide residue having a modified nucleobase in the target nucleic acid [e.g., refer to (I) in FIG. 17A]. The probe may be a probe lacking one nucleotide residue alone complementary with respect to the nucleotide residue having the modified nucleobase in the target nucleic acid [e.g., refer to (I-1) in FIG. 17B] or a probe lacking two or more (2 to 20, 2 to 10, or 2 to 5, for example) adjacent nucleotide residues including the nucleotide residue having the modified nucleobase in the target nucleic acid [e.g., refer to (I-2) in FIG. 17C]. The number of the nucleotide residue having the modified nucleobase in the unpaired part is not limited to a particular number so long as it is one or more (e.g., 1 to 20, 1 to 10, 1 to 5, or 1 to 3) as described above. Concerning the probe, refer to Patent Literature 1 and Non-Patent Literature 2, for example. When the position of the nucleotide residue having the modified nucleobase in the target nucleic acid to be measured is determined, such design is made possible.

Figure 18A:
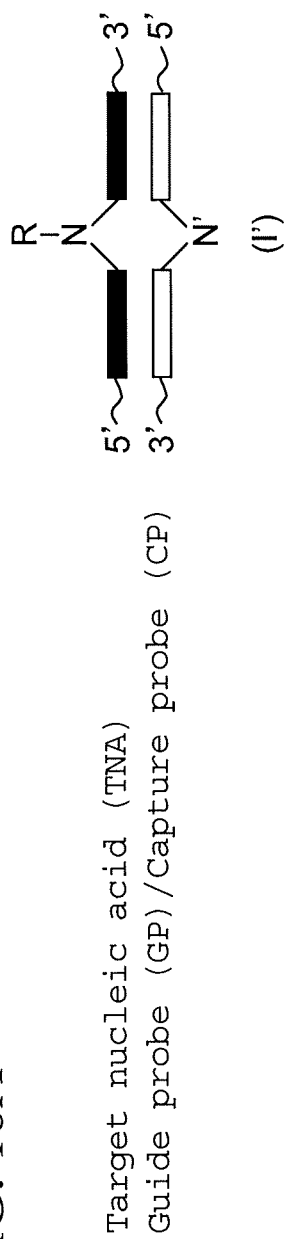
FIGS. 18A-18C show formations of unpaired part of modified nucleobase in double-stranded structure part including target nucleic acid and guide probe or capture probe in hybrid (2).
R-N: Nucleotide residue having a modified nucleobase
N: Nucleotide residue having a non-modified nucleobase, which composes a target nucleic acid
N': Nucleotide residue composing a guide probe or a capture probe
m in Nm: Number of nucleotide residues in non-complementary part (N1 to Nm) (e.g., 2 to 20. When m is 2, either N1 or N2 or both N1 and N2 may have substituent R)
m' in N'm': Number of nucleotide residues in non-complementary part (N'1 to N'm') (e.g., 2 to 20)
R: Substituent that nucleobase has
Figure 18B:
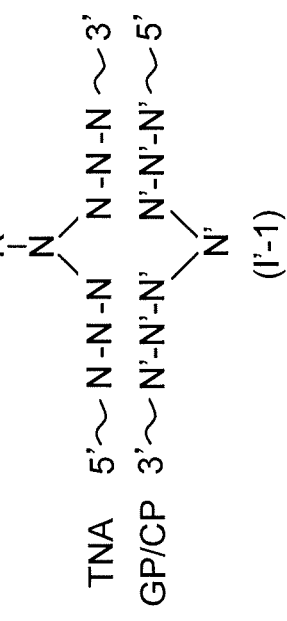
Figure 18C:
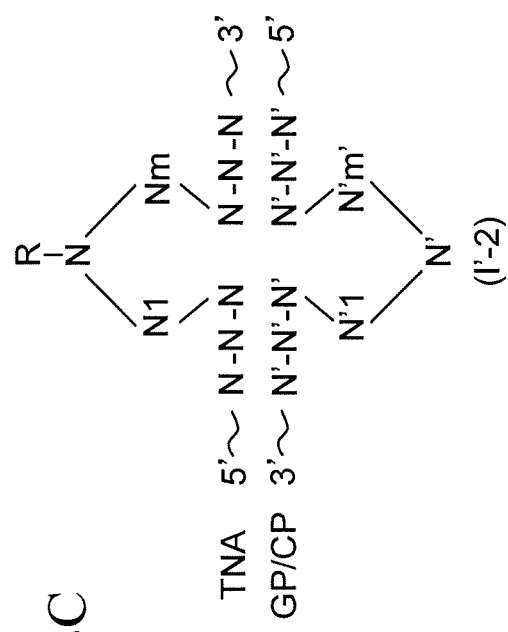

Another example of the probe in which the unpaired part of the modified nucleobase is formed in the (a) and (b) double-stranded structure parts is a probe having a nucleotide residue noncomplementary with respect to the nucleotide residue having the modified nucleobase in the target nucleic acid [e.g., refer to (I') in FIG. 18A]. The probe may be a probe having one nucleotide residue alone noncomplementary with respect to the nucleotide residue having the modified nucleobase in the target nucleic acid [e.g., refer to (I'-1) in FIG. 18B] or a probe in which two or more (2 to 20, 2 to 10, or 2 to 5, for example) adjacent nucleotide residues including the nucleotide residue having the modified nucleobase in the target nucleic acid are noncomplementary [e.g., refer to (I'-2) in FIG. 18C]. When the position of the nucleotide residue having the modified nucleobase in the target nucleic acid to be measured is determined, such design is made possible.

Figure 19A:
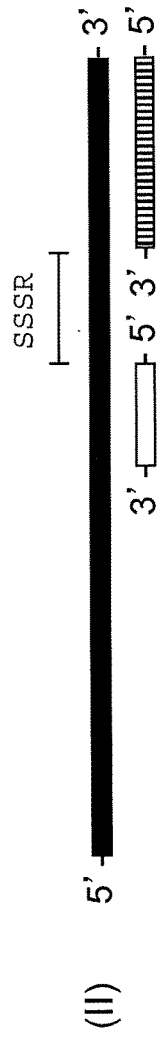
FIG. 19A-19C show another embodiment of the present invention, in which the guide probe and the capture probe may be designed so that a short single-stranded region (a non-hybridization short region) containing a nucleotide residue having a modified nucleobase in between the guide probe and the capture probe and/or in between a plurality of guide probes will be formed in the hybrid formed by the hybridization with the target nucleic acid. SSSR contains nucleotide residue having modified nucleobase
Figure 19B:
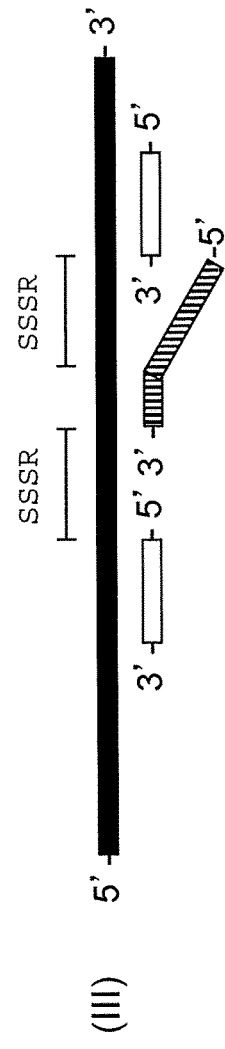
Figure 19C:

In another embodiment, the guide probe and the capture probe may be designed so that a short single-stranded region (a non-hybridization short region) containing a nucleotide residue having a modified nucleobase in between the guide probe and the capture probe and/or in between a plurality of guide probes will be formed in the hybrid formed by the hybridization with the target nucleic acid [e.g., refer to (II) to (IV) in FIGS. 19A-19C]. It is considered that the short single-stranded region present in between two or more hybridization regions formed by hybridization between two or more probes and the target nucleic acid can avoid Specific Problem 11 in that the non-hybridized region (the single-stranded region) of the target nucleic acid in the hybrid easily forms the secondary structure. The short single-stranded region containing the nucleotide residue having the modified nucleobase is not limited to a particular region so long as it contains the nucleotide residue having the modified nucleobase and it is a single-stranded region short enough to be unable to form a stable secondary structure by the method of the present invention and may be a region including 1 to 20, preferably 1 to 15, more preferably 1 to 10, and further more preferably 1, 2, 3, 4, or 5 full length nucleotide residues, for example. Guide Probes 1 and 2 in the example succeeded in the formation of the short single-stranded region including three or two nucleotide residues including the nucleotide residue having the modified nucleobase in the hybrid, for example. When the position of the nucleotide residue having the modified nucleobase in the target nucleic acid to be measured is determined, the probe can be designed so as to form the short single-stranded region containing the nucleotide residue having the modified nucleobase.

The method of the present invention may further include mixing the nucleic acid sample, the capture probe, and the guide probe in a solution to prepare a solution containing the nucleic acid sample, the capture probe, and the guide probe.

The concentration of the target nucleic acid in the incubation solution is not limited to a particular value so long as it is detectable by the method of the present invention and may be 0.001 nM or more, preferably 0.01 nM or more, 0.1 nM or more, or 1 nM or more, for example. The concentration of the target nucleic acid in the solution may also be 1 M or less, 100 mM or less, 10 mM or less, 1 mM or less, 100 µM or less, 10 µM or less, or 1 µM or less, for example. The concentration of the target nucleic acid in the nucleic acid sample is unknown in many cases, and it may be difficult to strictly set a concentration of the target nucleic acid. Depending on the type of the nucleic acid sample, the concentration of the target nucleic acid that can be contained in the nucleic acid sample can empirically be predicted to some extent, or the concentration of the target nucleic acid has been determined (in a case when, although the size and/or concentration of the target nucleic acid is separately measured, the presence or absence of the modified nucleobase in the target nucleic acid and the content of the modified nucleobase in the target nucleic acid are unknown, for example). In such cases, setting of the concentration of the target nucleic acid may be attempted as described above.

The concentration of the capture probe in the incubation solution is not limited to a particular value so long as the target nucleic acid is detectable by the method of the present invention and may be 0.1 nM or more, preferably 1 nM or more, and more preferably 10 nM or more, for example. The concentration of the capture probe in the solution may also be 1 M or less, 100 mM or less, 10 mM or less, 1 mM or less, 100 µM or less, 10 µM or less, or 1 µM or less, for example. Consequently, the capture probe may be added to the solution so that such a concentration will be achieved.

The concentration of the guide probe in the incubation solution is not limited to a particular value so long as the target nucleic acid is detectable by the method of the present invention and may be 0.1 nM or more, preferably 1 nM or more, and more preferably 10 nM or more, for example. The concentration of the capture probe in the solution may also be 1 M or less, 100 mM or less, 10 mM or less, 1 mM or less, 100 µM or less, 10 µM or less, or 1 µM or less, for example. Consequently, the guide probe may be added to the solution so that such a concentration will be achieved.

The concentration ratio between the capture probe and the guide probe in the incubation solution is not limited to a particular ratio so long as the modified nucleobase in the target nucleic acid can be measured. The concentration ratio (the capture probe to the guide probe) may be 1:100 to 100:1, 1:50 to 50:1, 1:20 to 20:1, or 1:10 to 10:1, for example. Alternatively, the capture probe may be used in a higher concentration than the guide probe.

The target nucleic acid may be a target nucleic acid optionally containing two or more modified nucleobases. The number of the modified nucleobases optionally composing the target nucleic acid is not limited to a particular number so long as it is two or more and is 2 to 30, 2 to 20, 2 to 10, or 2 to 5 (e.g., 2, 3, 4, or 5), for example. In a case where a plurality of modified nucleobases are contained in the target nucleic acid, even when the concentration of the target nucleic acid in the solution used for the hybridization is extremely low, the modified nucleobases can be measured with high sensitivity. Consequently, the method of the present invention can use a guide probe and/or a capture probe that are designed so as to hybridize with the target nucleic acid optionally containing two or more modified nucleobases. When the number of nucleobases optionally modified in the target nucleic acid to be measured is determined, such design is made possible.

In an embodiment, the nucleic acid sample is a sample containing a single-stranded target nucleic acid (preferably a target DNA) containing a modified nucleobase. In this case, step (1) may include performing incubation for a denaturation reaction of the single-stranded target nucleic acid in addition to performing incubation for the hybridization reaction of the single-stranded target nucleic acid, the capture probe, and the guide probe. The incubation for the hybridization reaction can be performed on the hybridization conditions described above, and the incubation for the denaturation reaction can be performed on the conditions of 1 minute to 30 minutes (preferably 2 minutes to 10 minutes) at 70° C. to 100° C. (preferably 80° C. to 98° C.), for example.

In another embodiment, the nucleic acid sample is a sample containing a double-stranded target nucleic acid (preferably a target DNA) containing a modified nucleobase. In this case, step (1) may include performing incubation for dissociation and denaturation reactions of the double-stranded target nucleic acid in addition to performing incubation for the hybridization reaction of the double-stranded target nucleic acid, the capture probe, and the guide probe. The incubation for the hybridization reaction can be performed on the hybridization conditions described above, and the incubation for the dissociation and denaturation reactions can be performed on the conditions of 1 minute to 30 minutes (preferably 2 minutes to 10 minutes) at 70° C. to 100° C. (preferably 80° C. to 98° C.), for example.

In a preferable embodiment, the nucleic acid sample, the capture probe, and the guide probe are incubated in the solution in the presence of a nucleic acid denaturant. The nucleic acid denaturant refers to a substance that has the capability of denaturating a nucleic acid by destroying a higher order structure of the nucleic acid. The concentration of the nucleic acid denaturant in the incubation solution is preferably set so as to increase detection sensitivity for the modified nucleobase in the target nucleic acid (especially, the double-stranded target nucleic acid). The concentration is a concentration exceeding 0.5 M and preferably 1 M or more, for example. The concentration may also be 20 M or less, 10 M or less, 8 M or less, 6 M or less, 4 M or less, 3 M or less, or 2.5 M or less. The nucleic acid denaturant may be a single type or a plurality of types (e.g., two or three types).

Examples of the nucleic acid denaturant includes chaotropic agents and electron donating compounds.

Examples of the chaotropic agents include a guanidinium ion, a barium ion, a calcium ion, a magnesium ion, a thiocyanate ion, a perchlorate ion, a nitrate ion, a bromine ion, an iodide ion, urea, and salts thereof (e.g., metallic salts, inorganic salts, and organic salts). The chaotropic agent is preferably guanidine thiocyanate, guanidine hydrochloride, or urea.

In the present invention, the electron donating compound refers to a compound containing an electron donating heteroatom having a nucleic acid denaturation effect. Examples of the heteroatom include a nitrogen atom, an oxygen atom, and a sulfur atom. The electron donating compound is preferably a heterocyclic compound having electron donating property. Examples of the heterocyclic compound include nonaromatic heterocyclic compounds and compounds having a π electron-excessive aromatic heterocycle (e.g., a five-membered aromatic heterocycle). Examples of the heterocyclic compound having electron donating property include monocyclic aromatic heterocyclic compounds having electron donating property and having a five-membered ring structure containing one or two or more heteroatoms in the ring (e.g., pyrrole, pyrazole, and imidazole), fused ring compounds thereof (e.g., indole and benzimidazole), and nonaromatic heterocyclic compounds having electron donating property and containing one or two or more heteroatoms in the ring (e.g., pyrrolidine, piperidine, and piperazine). The heteroatom is preferably a nitrogen atom.

In a more preferable embodiment, the nucleic acid sample, the capture probe, and the guide probe are incubated in the solution in the presence of both the nucleic acid denaturant and a surfactant. In this case, the nucleic acid denaturant and the concentration of the nucleic acid denaturant in the incubation solution are as described above. The concentration of the surfactant in the incubation solution is preferably set so as to reduce a background value of a detection signal. The concentration is 0.05% (v/v) or more, preferably 0.1% (v/v) or more, and more preferably 0.5% (v/v) or more, for example. The concentration may also be 20% (v/v) or less, 10% (v/v) or less, 8% (v/v) or less, 6% (v/v) or less, 4% (v/v) or less, or 2% (v/v) or less. The surfactant may be a single type or a plurality of types (e.g., two or three types).

Examples of the surfactant include anionic surfactants, cationic surfactants, amphoteric surfactants, and nonionic surfactants.

Examples of the anionic surfactants include hexyl sulfuric acid, octyl sulfuric acid, decyl sulfuric acid, dodecyl sulfuric acid, tetradecyl sulfuric acid, hexadecyl sulfuric acid, dodecyl phosphonic acid, dodecyl benzene sulfonic acid, n-lauroyl sarcosine, n-dodecanoyl sarcosine acid, and salts thereof (e.g. sodium salts).

Examples of the cationic surfactants include quaternary ammonium compounds (e.g., cetyldimethylethylammonium, hexadecyltrimethylammonium, hexadecyltrimethylammonium, and myristyltrimethylammonium), quaternary phosphonium compounds, and salts thereof (e.g., halides).

Examples of the amphoteric surfactants include Zwittergent, ASB-14, 3-N(N,N-dimethyloctylammonio)propane sulfonic acid, 3-n(N,N-dimethyloctylammonio)propane sulfonic acid, 3-(decyldimethylammonio)propane sulfonate acid, N-dodecyl-N,N-dimethyl-3-ammonio-1-propane sulfonic acid, 3-(N,N-dimethylmyristylammonio)propane sulfonic acid, 3-(N,N-dimethylpalmitylammonio)propane sulfonic acid, 3-(N,N-dimethyloctadecylammonio)propane sulfonic acid, and salts thereof.

Examples of the nonionic surfactants include Tween-series surfactants (e.g., Tween-20, Tween-40, Tween-60, and Tween-80), TritonX-series surfactants (e.g., TritonX-100), MEGA-series surfactants (e.g., Mega-8), and NP40.

The modified nucleobase is measured using an antibody against the modified nucleobase in a solution containing the hybrid. In the measurement, although the solution obtained at step (1) may be used as it is, addition of another solution and/or replacement of the solution with another solution may be performed in order to perform measurement in a solution more suitable for the measurement of the modified nucleobase by the antibody. The replacement can be performed by adding the solution obtained at step (1) to a solid phase, immobilizing the hybrid that can be contained in the solution to the solid phase, removing the solution from the solid phase, washing the solid phase with a cleaning liquid as needed, and adding another solution (e.g., a solution containing the antibody against the modified nucleobase) thereto, for example. The solution used in the measurement is not limited to a particular type so long as it is a solution suitable for an antigen-antibody reaction.

The measurement can be performed by immunological methodology. Examples of the immunological methodology include an enzyme immunoassay (EIA) (e.g., direct competitive enzyme-linked immunosorbent assay (ELISA), indirect competitive ELISA, and sandwich ELISA), a radioimmunoassay (RIA), a fluoroimmunoassay (FIA), immunochromatography, a luminescence immunoassay, a spin immunoassay, Western blot, and latex agglutination.

The antibody against the modified nucleobase may be a polyclonal antibody or a monoclonal antibody. The antibody against the modified nucleobase may be any isotype of immunoglobulin (e.g., IgG, IgM, IgA, IgD, IgE, and IgY). The antibody against the modified nucleobase may be a full-length antibody. The full-length antibody refers to an antibody containing a heavy chain and a light chain containing a variable region and a constant region, respectively (e.g., an antibody containing two Fab parts and an Fc part). The antibody against the modified nucleobase may also be an antibody fragment derived from the full-length antibody. The antibody fragment is part of the full-length antibody, and examples thereof include F(ab')$_2$, Fab', Fab, and Fv. The antibody against the modified nucleobase may also be a modified antibody such as a single-stranded antibody. The antibody against the modified nucleobase may further be an antibody used as a primary antibody in an immunoassay such as ELISA, and in this case, a secondary antibody is used in combination.

The antibody used against the modified nucleobase may have affinity for the modified nucleobase, a nucleoside having the modified nucleobase (a structural unit including the modified nucleobase and 2'-deoxyribose or ribose), a nucleotide having the modified nucleobase (a structural unit including the modified nucleobase, 2'-deoxyribose or ribose, and phosphate), or two or more nucleotides containing the nucleotide having the modified nucleobase (e.g., an oligonucleotide including two to five nucleotides). Examples of the antibody against the modified nucleobase when the target nucleic acid is DNA include 1) antibodies against a deoxyribonucleoside having a modified nucleobase selected from the group consisting of 2'-deoxy-modified adenosine, 2'-deoxy-modified guanosine, 2'-deoxy-modified cytidine, and 2'-deoxy-modified thymidine, 2) antibodies against a deoxyribonucleotide having a modified nucleobase selected from the group consisting of 2'-deoxy-modified adenosine 5'-phosphate, 2'-deoxy- modified guanosine 5'-phosphate, 2'-deoxy-modified cytidine 5'-phosphate, and 2'-deoxy-modified thymidine 5'-phosphate, and 3) antibodies against two or more deoxyribonucleotides containing the deoxyribonucleotide having the modified nucleobase. Examples of the antibody against the modified nucleobase when the target nucleic acid is RNA include 1') antibodies against a nucleoside having a modified nucleobase selected from the group consisting of modified adenosine, modified guanosine, modified cytidine, and modified uridine, 2') antibodies against a ribonucleotide having a modified nucleobase selected from the group consisting of modified adenosine 5'-phosphate, modified guanosine 5'-phosphate, modified cytidine 5'-phosphate, and modified uridine 5'-phosphate and 3') antibodies against two or more ribonucleotides including the ribonucleotide having the modified nucleobase. Alternatively, as the antibody against the modified nucleobase, an antibody that binds to a double-stranded target nucleic acid containing a nucleotide residue having a modified nucleobase described in WO2007/119518 may be used.

For the antibody against the modified nucleobase, an antibody prepared by using a complex of the modified nucleobase, the nucleoside having the modified nucleobase, the nucleotide having the modified nucleobase, or the two or more nucleotides including the nucleotide having the modified nucleobase and a carrier protein (e.g., BSA and KLH) as an antigen can be used, for example. Various antibodies against the modified nucleobase prepared using such complexes are commercially available, and the method of the present invention may use a commercially available antibody, for example. The method of the present invention may also use the antibody against the modified nucleobase prepared as follows, for example.

The polyclonal antibody against the modified nucleobase can be acquired by administering the complex as the antigen together with a commercially available adjuvant (e.g., a complete or incomplete Freund's adjuvant) to an animal subcutaneously or intra-abdominally about two to four times every 2 to 3 weeks, collecting whole blood about 3 to about 10 days after the final immunity, and purifying an antiserum, for example. Examples of the animal to which the antigen is administered include mammals such as rats, mice, rabbits, goats, cattle, guinea pigs, and hamsters.

The monoclonal antibody against the modified nucleobase can be prepared by cell fusion, for example. The complex is administered together with a commercially available adjuvant to a mouse subcutaneously or intra-abdominally two to four times, collecting the spleen or a lymph node about three days after the final administration, and collecting white blood cells, for example. These white blood cells and a myeloma cell (e.g., NS-1) are subjected to cell fusion to obtain a hybridoma producing a monoclonal antibody against the factor. Examples of the cell fusion include a PEG method and a voltage pulse method. The hybridoma producing a desired monoclonal antibody can be selected by detecting an antibody that specifically binds to an antigen using known EIA, RIA, or the like in cultivated supernatant. Cultivation of the hybridoma producing the monoclonal antibody can be performed in vitro or in vivo such as in a mouse, a rat, or preferably mouse ascites, and the antibody can be acquired from the cultivated supernatant of the hybridoma or animal ascites. The monoclonal antibody may be any isotype of IgG, IgM, IgA, IgE, and the like. Alternatively, in vitro methods such as a phage display method (Ulman et al, Proc. Natl. Acad. Sci. U.S.A., 90, 1184-89 (1993)) and an ADLib system (WO2004/011644) are also known as methods for preparing a monoclonal antibody, and such methods may be used to prepare the antibody against the modified nucleobase.

The antibody against the modified nucleobase may be used while being immobilized to a solid phase. Examples of the solid phase include supports such as particles (e.g., magnetic particles), membranes (e.g., a nitrocellulose membrane), glass, plastic, and metal, containers such as plates (e.g., a multiwell plate), and devices. The antibody may also be provided in the form of being impregnated into a medium such as filter paper. The antibody against the modified nucleobase may be labeled with a labeling substance. Examples of the labeling substance include enzymes (e.g., peroxidase, alkaline phosphatase, luciferase, and β-galactosidase), affinity substances (e.g., streptavidin and biotin), fluorescent substances or proteins (e.g., fluorescein, fluorescein isothiocyanate, rhodamine, green fluorescent protein, and red fluorescent protein), luminescent substances (e.g., luciferin and aequorin), and radioactive substances (e.g., $^3$H, $^{14}$C, $^{32}$P, $^{35}$S, and $^{125}$I). When a secondary antibody is used in the method of the present invention, the secondary antibody may be labeled with such a labeling substance.

The measurement of the modified nucleobase by the antibody against the modified nucleobase is performed qualitatively or quantitatively, whereby the presence or absence or the amount of the modified nucleobase can be evaluated. The measurement of the modified nucleobase by the antibody against the modified nucleobase may be performed by forming a unpaired structure (a bulge structure) in between the target nucleic acid and the probe and then measuring the modified nucleobase in the unpaired structure by the antibody against the modified nucleobase as described in Patent Literature 1 and Non-Patent Literature 1 and 2, for example. Alternatively, the measurement of the modified nucleobase by the antibody against the modified nucleobase may be performed using the antibody that binds to the double-stranded target nucleic acid containing the nucleotide residue having the modified nucleobase described in WO2007/119518. In the present invention, the measurement of the modified nucleobase can intend not only the measurement of the modified nucleobase itself but also the measurement of the target nucleic acid containing the modified nucleobase.

The measurement of the presence or absence of the modified nucleobase may be performed as follows, for example:

(2-1) In the solution obtained at step (1), performing an assay using the antibody against the modified nucleobase to measure a signal value;

(2-2) In a solution that does not contain the target nucleic acid containing the modified nucleobase and contains the capture probe and the guide probe, performing an assay using the antibody against the modified nucleobase to measure a background value; and (2-3) comparing the signal value with the background value to evaluate the presence or absence of the modified nucleobase.

In the measurement of the modified nucleobase, the signal value and the background value are values (e.g., absorbance, the degree of fluorescence, the degree of coloration, and radioactivity) that are measured using a label binding to the antibody against the modified nucleobase or the secondary antibody (when the secondary antibody is used).

The measurement of the amount of the modified nucleobase may be performed together with the measurement of the background value, for example. Specifically, the measurement of the amount of the modified nucleobase may be performed as follows:

(2-1') In the solution obtained at step (1), performing an assay using the antibody against the modified nucleobase to measure a signal value;

(2-2') In a solution that does not contain the target nucleic acid containing the modified nucleobase and contains the capture probe and the guide probe, performing an assay using the antibody against the modified nucleobase to measure a background value;

(2-3') correcting the signal value with the background value to obtain a corrected signal value; and (2-4') based on the corrected signal value, evaluating the amount of the modified nucleobase.

Alternatively, the measurement of the amount of the modified nucleobase may be performed using a preparation. Specifically, the measurement of the amount of the modified nucleobase may be performed as follows:

(2-1") In the solution obtained at step (1), performing an assay using the antibody against the modified nucleobase to measure a signal value;

(2-2") In a solution containing the target nucleic acid containing the modified nucleobase (preparation), the capture probe, and the guide probe, performing an assay using the antibody against the modified nucleobase to measure a value for calibration; and (2-3") Comparing the signal value with the value for calibration to evaluate the amount of the modified nucleobase.

The measurement using the preparation may be performed in combination with the measurement of the background value.

In a specific embodiment, the method of the present invention may be performed as follows:

(i) incubating the nucleic acid sample containing the target nucleic acid containing the modified nucleobase and a capture probe labeled with a first affinity substance and a guide probe in a solution to form a hybrid including the target nucleic acid, the capture probe, and the guide probe;

(ii) immobilizing the hybrid to a solid phase treated with a second affinity substance;

(iii) reacting a primary antibody against the modified nucleobase with the hybrid immobilized to the solid phase to obtain a primary complex of the primary antibody and the hybrid;

(iv) reacting a secondary antibody labeled with a labeling substance with the primary complex to obtain a secondary complex of the secondary antibody and the primary antibody; and (v) using the labeling substance that the secondary antibody in the secondary complex has, measuring the presence and/or the amount of the formed hybrid (in other words, the modified nucleobase).

The first affinity substance and the second affinity substance are used in a combination having mutual affinity (e.g., a combination of biotin and streptavidin). The method of the present invention may include (i') incubating the nucleic acid sample containing the target nucleic acid containing the modified nucleobase, the capture probe immobilized to a solid phase, and the guide probe in a solution to form a hybrid including the target nucleic acid, the capture probe, and the guide probe in place of steps (i) and (ii). In this case, obtaining the capture probe immobilized to the solid phase (e.g., adding the capture probe labeled with the first affinity substance to the solid phase treated with the second affinity substance) may further be included. The method of the present invention may also include washing the solid phase before step (iii). The secondary antibody may be an antibody that recognizes the primary antibody alone (e.g., an antibody that binds to the constant region of the primary antibody) and may also be an antibody that recognizes both the primary antibody in the secondary complex and the primary complex. In addition, the method of the present invention including (i) to (v) can be performed in accordance with the methodology described in detail in the specification.

The present invention also provides a kit for measuring a modified nucleobase. The kit of the present invention includes:

(I) a guide probe; and
(II) a capture probe and/or an antibody against a modified nucleobase.

The guide probe, the capture probe, and the antibody against the modified nucleobase are as described above. The capture probe may be labeled with the affinity substance, and the antibody against a modified nucleobase may be labeled with the labeling substance, for example. The kit of the present invention may further contain the above components such as the affinity substance, the labeling substance, the secondary antibody, a detection reagent for the secondary antibody (e.g., when the secondary antibody is labeled with an enzyme, a substrate for the enzyme), and the solid phase. The solid phase may be treated with the affinity substance. The kit of the present invention may also contain a preparation of the modified nucleobase or a preparation of the target nucleic acid containing the modified nucleobase as a solution or as powder. The kit of the present invention preferably contains the guide probe, the capture probe, and the antibody against the modified nucleobase. The kit of the present invention may further contain the nucleic acid denaturant described above. The kit of the present invention may further contain the surfactant described above.

The kit of the present invention contains the components in the form of being isolated from each other or in the form of being mixed with each other. In the kit of the present invention, the components may be provided in the form of being contained in different containers (e.g., a tube and a plate), for example, and the capture probe and the guide probe may be provided in the form of being mixed with each other (e.g., in the same solution), for example. Alternatively, the kit of the present invention may be provided in the form of a device. Specifically, all the components may be provided in the form of being contained in a device. Alternatively, part of the components may be provided in the form of being contained in a device, whereas the rest may be provided in the form of not being contained in the device (e.g., the form of being contained in a different container). In this case, the components not contained in the device may be used by being injected into the device in the measurement of a target substance.

EXAMPLES

Although the following describes the present invention in more detail with reference to examples, the present invention is not limited to these examples.

Reference Example 1

Measurement of Modified Nucleobase in Target Nucleic Acid by Capture Probe 1-1) Preparation of Target Nucleic Acid The target nucleic acid was prepared in accordance with the following procedure.

Polymerase chain reaction (PCR) was used for the preparation of the target nucleic acid. KOD Plus (Product No. KOD-201) manufactured by Toyobo Co., Ltd. was used for an enzyme for PCR. A forward primer: 5'-TAGAACGCTTTGCGTCCCGAC-3' (SEQ ID NO: 1) and a reverse primer: 5'-CTGCAGGACCACTCGAGGCTG-3' (SEQ ID NO: 2) artificially synthesized by Hokkaido System Science Co., Ltd. were used for two kinds of primers for nucleic acid amplification. A protocol for PCR amplification was 30 cycles of one set including heating at 94° C. for 2 minutes, 94° C. for 15 seconds, 55° C. for 30 seconds, and 68° C. for 1 minute.

After performing PCR amplification using a nucleic acid (nucleotide sequence: 5'-TAGAACGCTTTGCGTCCCGACGCCCGCAGGTCCTCGCGGTGCGCACCGTTTGCGACTTGGTGAGTGTCTGGGTCGCCTCGCTCCCGGAAGAGTGCGGAGCTCTCCCTCGGGACGGTGGCAGCCTCGAGTGGTCCTGCA-3' (SEQ ID NO: 3)) artificially synthesized by Hokkaido System Science Co., Ltd. as a template, purification was performed using QIAquick PCR Purification Kit of Qiagen to prepare a 138-bp nucleic acid.

In order to methylate cytosine of CpG within the 138-bp nucleic acid prepared as described above, treatment with CpG Methyltransferase (M. SssI) (Product No. EM0821) of Thermo Scientific was performed. A reaction solution was prepared in accordance with an attached document. The reaction solution was reacted at 37° C. for 20 minutes, was further reacted at 65° C. for 20 minutes, and was purified using QIAquick Nucleotide Removal Kit of Qiagen to obtain a target nucleic acid (a methylated double-stranded DNA including the nucleotide sequence of SEQ ID NO: 3).

1-2) Measurement of Modified Nucleobase in Single-Stranded and Double-Stranded Target Nucleic Acids by Capture Probe The nucleotide sequence of the capture probe for the target nucleic acid is 5'-UGCAGGACCACUCGAGGCUGCCAC-3' (SEQ ID NO: 4) (the backbone of the nucleic acid is 2'-O-methylated RNA, the 5'-end is biotin-labeled); that artificially synthesized by Hokkaido System Science Co., Ltd. was used. As target nucleic acids containing 5-methylcytosine, a single-stranded target nucleic acid (a methylated single-stranded DNA including the nucleotide sequence of SEQ ID NO: 3) artificially synthesized by Hokkaido System Science Co., Ltd. and a double-stranded target nucleic acid (a methylated double-stranded DNA including the nucleotide sequence of SEQ ID NO: 3) prepared in Reference Example 1-1) were used.

First, the target nucleic acid containing 5-methylcytosine (100 fmol, 10 fmol, 1 fmol, 0.1 fmol, or 0.01 fmol) and the capture probe (5 pmol) were dissolved in 100 µL of a hybridization buffer solution (5×SSC, 0.1% (v/v) Tween20). The solution was subjected to a reaction [a denaturation reaction (the single-stranded target nucleic acid) or dissociation and denaturation reactions (the double-stranded target nucleic acid)] at 95° C. for 5 minutes and was subjected to a hybridization reaction at 37° C. for 1 hour to form a hybrid of the target nucleic acid and the capture probe. A solution not containing the target nucleic acid was also prepared, and a similar operation was performed. To the solution after the hybridization reaction, 50 µL of magnetic particles coated with 375 µg/mL of streptavidin (Dynabeads M-280 Streptavidin manufactured by Invitrogen) were added and were reacted at 37° C. for 30 minutes to immobilize the nucleic acid hybrid to the magnetic particles. The nucleic acid hybrid immobilized to the magnetic particles was washed with 250 µL of TBS-T three times, and 100 ng/mL of an anti-methylcytosine antibody (Clone33D3 manufactured by Nippon Gene Co., Ltd.) was added thereto by 125 µL each and was reacted at 37° C. for 1 hour. The reactant was washed with 250 µL of TBS-T three times, and 250 ng/mL of an alkaline phosphatase-labeled anti-IgG antibody (manufactured by Millipore Corporation) was added thereto by 125 µL each and was reacted at 37° C. for 30 minutes. The reactant was washed with 250 µL of TBS-T three times, and a solution of a chemiluminescent substrate AMPPD was added thereto by 110 µL each and was reacted at 37° C. for 5 minutes. Thereafter, luminescence counts were measured by a microplate reader (Arvo manufactured by PerkinElmer Inc.).

Figure 4:
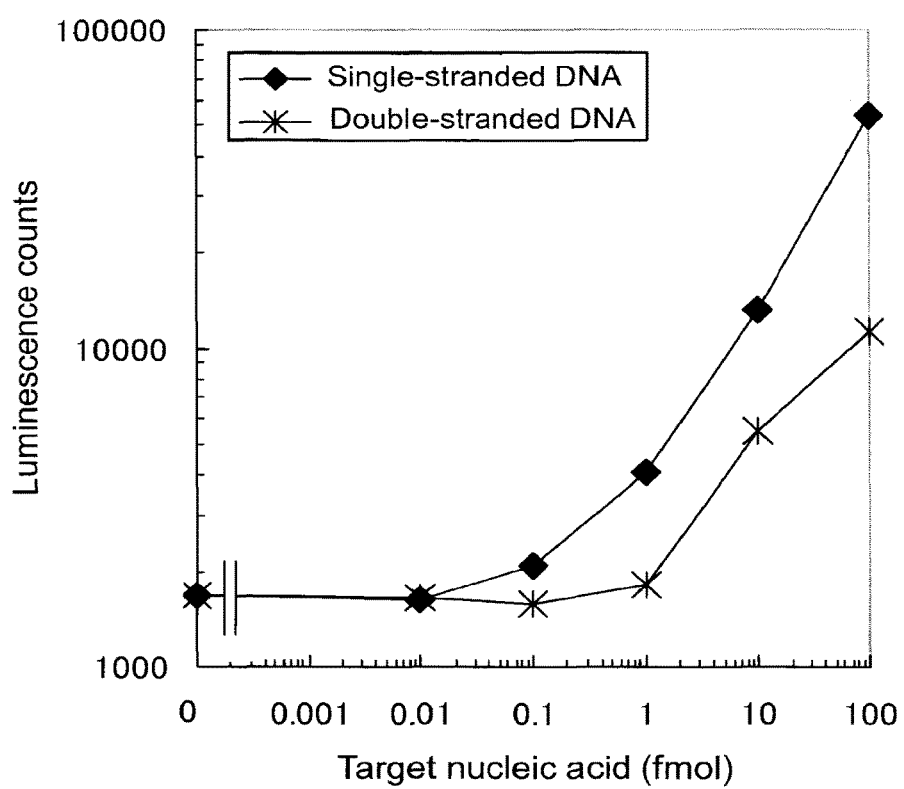
FIG. 4 is a diagram of the measurement of the modified nucleobase in the single-stranded and double-stranded target nucleic acids by the capture probe.

As a result of the measurement, the double-stranded target nucleic acid was lower in the luminescence counts than the single-stranded target nucleic acid, and the double-stranded target nucleic acid was captured to the magnetic particles in an amount only about one-tenth of the single-stranded target nucleic acid (Table 1 and FIG. 4). This phenomenon can be understood by the fact that the luminescence counts measured when the amount of the double-stranded target nucleic acid was 100 fmol was substantially equal to the luminescence counts measured when the amount of the single-stranded target nucleic acid was 10 fmol, for example (Table 1 and FIG. 4). This fact indicates that a capture rate for the double-stranded target nucleic acid by the capture probe (a hybrid formation rate) is lower than that of the single-stranded target nucleic acid.

TABLE 1

Measurement of modified nucleobase in single-stranded and double-stranded target nucleic acids by capture probe

|  | Amount of target nucleic acid | Luminescence counts | S/N |
|---|---|---|---|
| Single-stranded DNA | 100 fmol | 53945 | 32.15 |
|  | 10 fmol | 13140 | 7.83 |
|  | 1 fmol | 4079 | 2.43 |
|  | 0.1 fmol | 2083 | 1.24 |
|  | 0.01 fmol | 1628 | 0.97 |
|  | 0 mol | 1678 |  |
| Double-stranded DNA | 100 fmol | 11230 | 6.69 |
|  | 10 fmol | 5497 | 3.28 |
|  | 1 fmol | 1806 | 1.08 |
|  | 0.1 fmol | 1584 | 0.94 |

TABLE 1-continued

Measurement of modified nucleobase in single-stranded and double-stranded target nucleic acids by capture probe

|  | Amount of target nucleic acid | Luminescence counts | S/N |
|---|---|---|---|
|  | 0.01 fmol | 1650 | 0.98 |
|  | 0 mol | 1678 |  |

Luminescence counts of amount of target nucleic acid (fmol)/luminescence counts in the absence (that is, 0 mol) of target nucleic acid (the same hereinafter unless otherwise specified)

From the foregoing, Specific Problem I has been revealed.

Example 1

Measurement of Modified Nucleobase in Single-Stranded Target Nucleic Acid Using Capture Probe and Guide Probe 1-1) Measurement Using Capture Probe and Guide Probe The nucleotide sequence of the capture probe for the target nucleic acid is the nucleotide sequence of SEQ ID NO: 4 (the backbone of the nucleic acid is 2'-O-methylated RNA, the 5'-end is biotin-labeled), and the nucleotide sequence of the guide probe is 5'-CCCAGGGAGAGCTC-CCACTCTTCCGGAGCAGGCACCCAGACACTCAC-CAAGTCCAAACGTGCCACCCAGGACCTGCG-GCTCGGACCAAAGCTTCTA-3' (SEQ ID NO: 5) (Guide Probe 1); those artificially synthesized by Hokkaido System Science Co., Ltd. were used. Guide Probe 1 was designed so as to be able to hybridize with the target nucleic acid in a region different from a region with which the capture probe hybridizes in the target nucleic acid. As the target nucleic acid containing 5-methylcytosine, the single-stranded target nucleic acid (the methylated single-stranded DNA including the nucleotide sequence of SEQ ID NO: 3) artificially synthesized by Hokkaido System Science Co., Ltd. was used.

First, the target nucleic acid containing 5-methylcytosine (10 fmol or 1 fmol), the capture probe (5 pmol), and the guide probe (1 pmol) were dissolved in 100 µL of the hybridization buffer solution (5×SSC, 0.1% (v/v) Tween20). The solution was subjected to a denaturation reaction at 95° C. for 5 minutes and was subjected to a hybridization reaction at 37° C. for 1 hour to form a hybrid including the target nucleic acid, the capture probe, and the guide probe. A solution not containing the target nucleic acid was also prepared, and a similar operation was performed. To the solution after the hybridization reaction, 50 µL of the magnetic particles coated with 375 µg/mL of streptavidin (Dynabeads M-280 Streptavidin manufactured by Invitrogen) were added and were reacted at 37° C. for 30 minutes to immobilize the nucleic acid hybrid to the magnetic particles. The nucleic acid hybrid immobilized to the magnetic particles was washed with 250 µL of TBS-T three times, and 100 ng/mL of the anti-methylcytosine antibody (Clone33D3 manufactured by Nippon Gene Co., Ltd.) was added thereto by 125 µL each and was reacted at 37° C. for 1 hour. The reactant was washed with 250 µL of TBS-T three times, and 250 ng/mL of the alkaline phosphatase-labeled anti-IgG antibody (manufactured by Millipore Corporation) was added thereto by 125 µL each and was reacted at 37° C. for 30 minutes. The reactant was washed with 250 µL of TBS-T three times, and a solution of the chemiluminescent substrate AMPPD was added thereto by 110 µL each and was reacted at 37° C. for 5 minutes. Thereafter, luminescence counts were measured by the microplate reader (Arvo manufactured by PerkinElmer, Inc.).

1-2) Measurement Using Capture Probe (Conventional Method not Using Guide Probe)

Tests were carried out by a method similar to that in Example 1-1) except that the guide probe was not added.

1-3) Results

Figure 5:
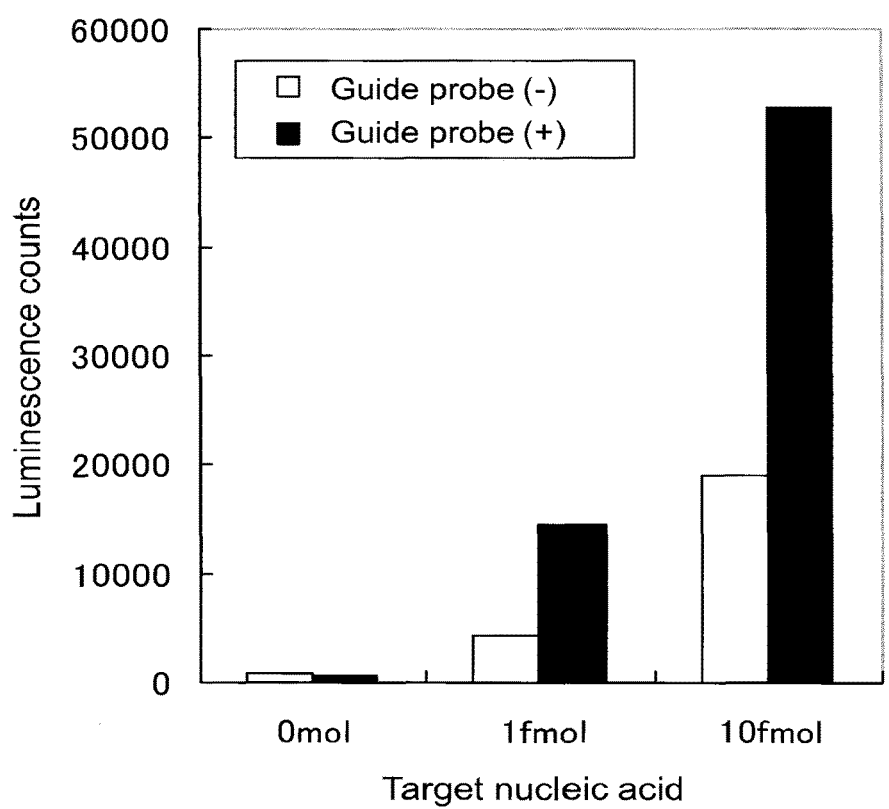
FIG. 5 is a diagram of the measurement of the modified nucleobase in the single-stranded target nucleic acid using the capture probe and a guide probe. Guide probe (−): the capture probe alone; and guide probe (+): the capture probe and the guide probe.

The luminescence counts measured using the guide probe remarkably increased compared with the luminescence counts measured without using the guide probe (Table 2 and FIG. 5).

Figure 3:
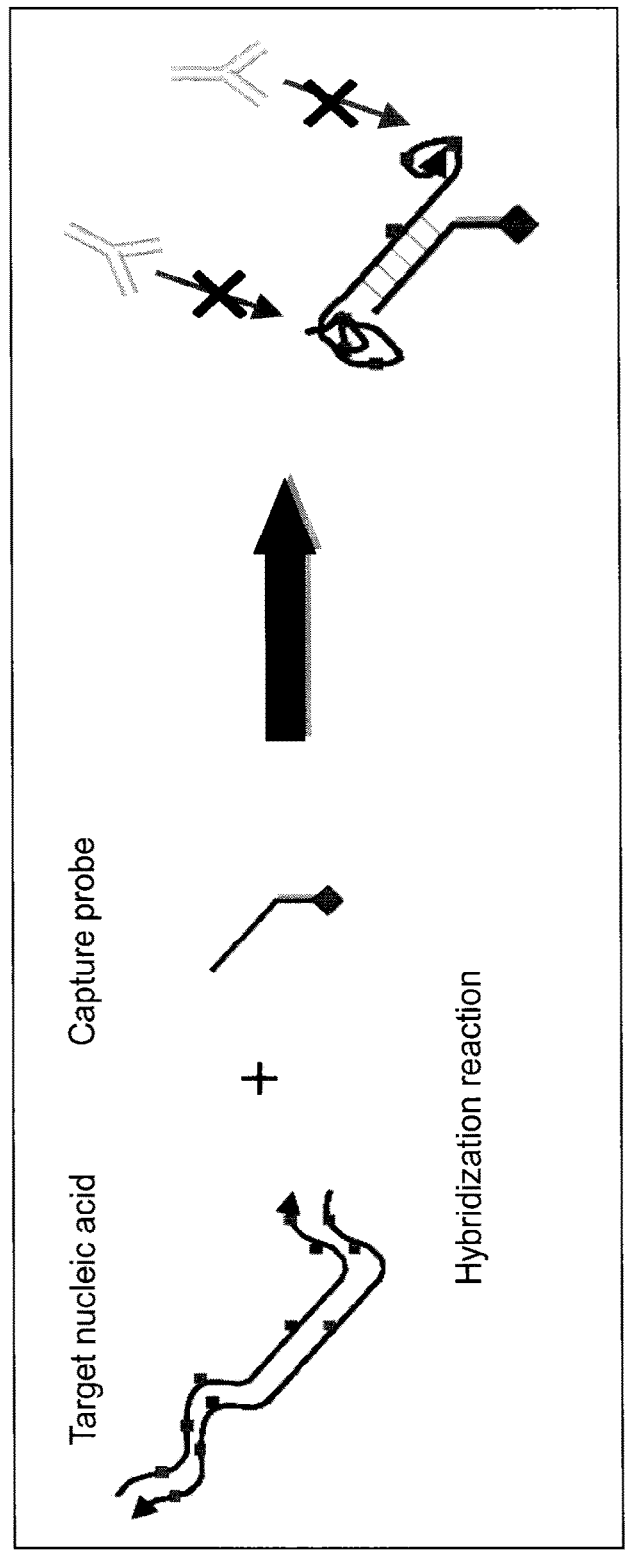
FIG. 3 is a diagram of an overview of a problem (Specific Problem II) related to the measurement of the modified nucleobase. In a conventional method for measuring the modified nucleobase in the target nucleic acid using the capture probe, a hybrid including the target nucleic acid and the capture probe is formed. The conventional method has a potential problem in that a non-hybridized region (a single-stranded region) in this hybrid forms a secondary structure, whereby the modified nucleobase contained in this secondary structure is difficult to be measured (in other words, detection sensitivity is low).

The fact that the luminescence counts increased by the formation of the hybrid of the single-stranded target nucleic acid and the guide probe indicates that the single-stranded target nucleic acid captured to the solid phase (the magnetic particles) via the capture probe forms the secondary structure in the absence of the guide probe and that it is difficult for the antibody to recognize the modified nucleobase in the secondary structure (FIG. 3). In other words, it is considered that Specific Problem II was potentially present.

It has been revealed that the guide probe hybridizes with a non-hybridized region (a single-stranded region that can form the secondary structure in the absence of the guide probe) in the hybrid including the single-stranded target nucleic acid and the capture probe, thereby enabling the secondary structure to be loosened, thereby enabling the antibody to efficiently recognize the modified nucleobase (in other words, an increase in detection sensitivity) (refer to Table 2 and FIG. 5). In other words, Specific Problem II has been solved using the guide probe.

TABLE 2

Measurement of modified nucleobase in single-stranded target nucleic acid using capture probe and guide probe

| Guide probe | Amount of target nucleic acid | Luminescence counts | S/N |
|---|---|---|---|
| − | 10 fmol | 18984 | 22.93 |
|  | 1 fmol | 4259 | 5.14 |
|  | 0 mol | 828 |  |
| + | 10 fmol | 52777 | 75.34 |
|  | 1 fmol | 14397 | 20.55 |
|  | 0 mol | 701 |  |

−: Example 1-2) Without using guide probe
+: Example 1-1) Using guide probe

From the foregoing, it has been revealed that the guide probe can increase detection sensitivity for the modified nucleobase in the single-stranded target nucleic acid.

Example 2

Measurement of Modified Nucleobase in Double-Stranded Target Nucleic Acid Using Capture Probe and Guide Probe 2-1) Measurement Using Capture Probe and Guide Probe Tests were carried out by a method similar to that in Example 1 except that the double-stranded target nucleic acid prepared in Reference Example 1-1) was used as the target nucleic acid containing 5-methylcytosine.

2-2) Measurement Using Capture Probe (without Using Guide Probe)

Tests were carried out by a method similar to that in Example 2-1) except that the guide probe was not added.

2-3) Results

Figure 6:
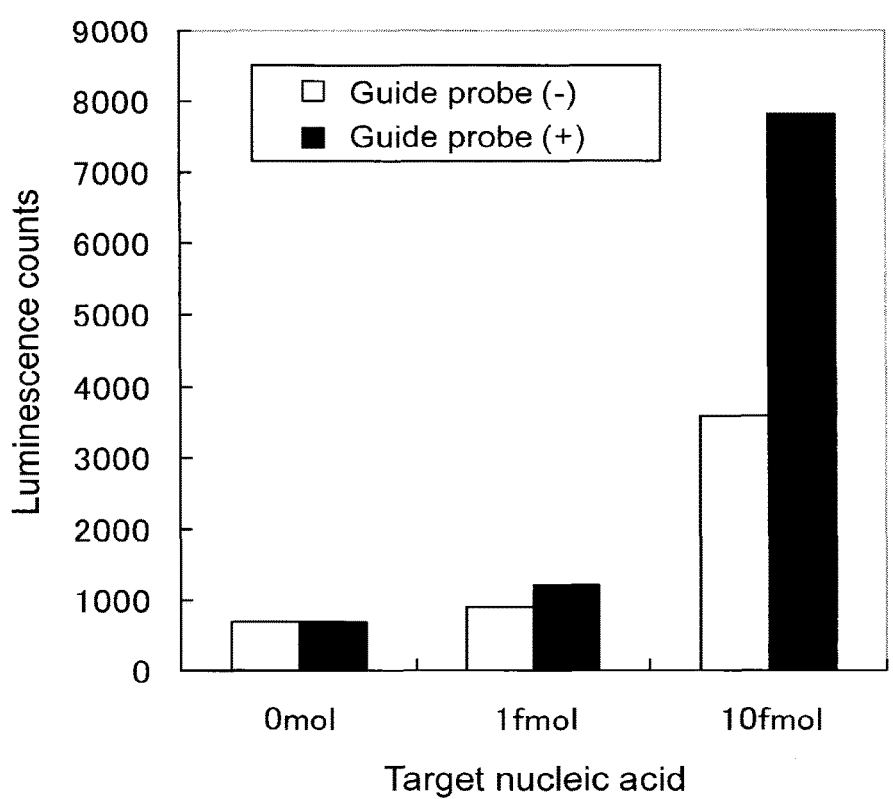
FIG. 6 is a diagram of the measurement of the modified nucleobase in the double-stranded target nucleic acid using the capture probe and the guide probe. Guide probe (−): the capture probe alone; and guide probe (+): the capture probe and the guide probe.

Also in the double-stranded target nucleic acid, the effect of addition of the guide probe was revealed similarly to the single-stranded target nucleic acid (Table 3 and FIG. 6). It is considered that this is because the complementary strand and the capture probe that were competing against each other for the target nucleic acid tended to form the hybrid of the target nucleic acid, the capture probe, and the guide probe through the addition of the guide probe. At the same time, it is considered that this is because even in the double-stranded target nucleic acid the non-hybridized region occurring when forming the hybrid with the capture probe hybridizes with the guide probe, whereby the formation of the secondary structure can be avoided.

TABLE 3

Measurement of modified nucleobase in double-stranded target nucleic acid using capture probe and guide probe

| Guide probe | Amount of target nucleic acid | Luminescence counts | S/N |
|---|---|---|---|
| − | 10 fmol | 3577 | 5.22 |
|  | 1 fmol | 917 | 1.34 |
|  | 0 mol | 686 |  |
| + | 10 fmol | 7827 | 11.29 |
|  | 1 fmol | 1215 | 1.75 |
|  | 0 mol | 693 |  |

−: Example 2-2) Without using guide probe
+: Example 2-1) Using guide probe

From the foregoing, it has been revealed that the guide probe can increase detection sensitivity for the modified nucleobase in the double-stranded target nucleic acid.

Example 3

Measurement of Modified Nucleobase in Double-Stranded Target Nucleic Acid Using Guide Probe in the Presence of Chaotropic Agent 3-1) Measurement Using Guide Probe in the Presence of Chaotropic Agent The nucleotide sequence of the capture probe for the target nucleic acid is the nucleotide sequence of SEQ ID NO: 4 (the backbone of the nucleic acid is 2'-O-methylated RNA, the 5'-end is biotin-labeled), and the nucleotide sequence of the guide probe is the nucleotide sequence of SEQ ID NO: 5 (Guide Probe 1); those artificially synthesized by Hokkaido System Science Co., Ltd. were used. As the target nucleic acid containing 5-methylcytosine, the double-stranded target nucleic acid prepared in Reference Example 1-1) was used. As a chaotropic agent, guanidine thiocyanate was used.

First, the double-stranded target nucleic acid containing 5-methylcytosine (10 fmol or 1 fmol), the capture probe (5 pmol), and the guide probe (1 pmol) were dissolved in 100 µL of a guanidine thiocyanate (+) buffer solution (100 mM of Tris-HCl, 4.2 M of guanidine thiocyanate, and 50 mM of EDTA.2Na). The solution was subjected to dissociation and denaturation reactions at 95° C. for 5 minutes and was subjected to a hybridization reaction at 37° C. for 1 hour to form a hybrid including the target nucleic acid, the capture probe, and the guide probe. A solution not containing the target nucleic acid was also prepared, and a similar operation was performed. To the solution after the hybridization reaction, 50 µL of the magnetic particles coated with 375

μg/mL of streptavidin (Dynabeads M-280 Streptavidin manufactured by Invitrogen) were added and were reacted at 37° C. for 30 minutes to immobilize the hybrid to the magnetic particles. The hybrid immobilized to the magnetic particles was washed with 250 μL of TBS-T three times, and 100 ng/mL of the anti-methylcytosine antibody (Clone33D3 manufactured by Nippon Gene Co., Ltd.) was added thereto by 125 μL each and was reacted at 37° C. for 1 hour. The reactant was washed with 250 μL of TBS-T three times, and 250 ng/mL of the alkaline phosphatase-labeled anti-IgG antibody (manufactured by Millipore Corporation) was added thereto by 125 μL each and was reacted at 37° C. for 30 minutes. The reactant was washed with 250 μL of TBS-T three times, and a solution of the chemiluminescent substrate AMPPD was added thereto by 110 μL each and was reacted at 37° C. for 5 minutes. Thereafter, luminescence counts were measured by the microplate reader (Arvo manufactured by PerkinElmer, Inc.).

3-2) Measurement Using Guide Probe [in the Absence of Chaotropic Agent (1)]

Tests were carried out by a method similar to that in 3-1) except that the hybridization buffer solution (5×SSC, 0.1% (v/v) Tween20) was used when the hybrid including the target nucleic acid, the capture probe, and guide probe was formed.

3-3) Measurement Using Guide Probe [in the Absence of Chaotropic Agent (2)]

Tests were carried out by a method similar to that in 3-1) except that a guanidine thiocyanate (−) buffer solution (100 mM of Tris-HCl and 50 mM of EDTA.2Na) was used when the hybrid including the target nucleic acid, the capture probe, and guide probe was formed.

3-4) Results

Figure 7:
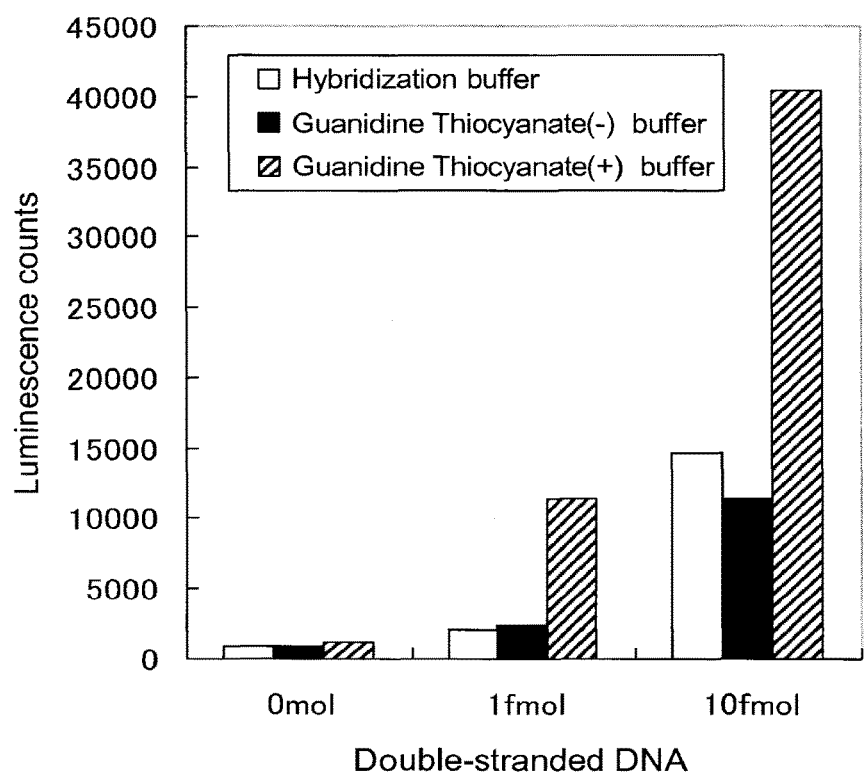
FIG. 7 is a diagram of the measurement of the modified nucleobase in the double-stranded target nucleic acid using the guide probe in the presence of a chaotropic agent. Hybridization buffer: the guide probe is used; guanidine thiocyanate (−) buffer: the guide probe is used; and guanidine thiocyanate (+) buffer: the guide probe is used in the presence of the chaotropic agent.

When the hybridization reaction was performed on the condition containing the chaotropic agent, the luminescence counts remarkably increased (Table 4 and FIG. 7). This fact indicates that the formation of the hybrid of the double-stranded target nucleic acid and the guide probe is facilitated to increase efficiency of capturing the target nucleic acid to the solid phase (the magnetic particles).

TABLE 4

Measurement of modified nucleobase in double-stranded target nucleic acid using guide probe in the presence of chaotropic agent

| Buffer solution condition | Amount of target nucleic acid | Luminescence counts | S/N |
|---|---|---|---|
| Hybridization buffer solution | 10 fmol | 14693 | 17.47 |
| | 1 fmol | 2048 | 2.44 |
| | 0 mol | 841 | |
| Guanidine thiocyanate (−) | 10 fmol | 11445 | 13.99 |
| | 1 fmol | 2307 | 2.82 |
| | 0 mol | 818 | |
| Guanidine thiocyanate (+) | 10 fmol | 40344 | 32.28 |
| | 1 fmol | 11329 | 9.06 |
| | 0 mol | 1250 | |

Hybridization buffer solution: Example 3-2) In the absence of chaotropic agent (1)
Guanidine thiocyanate (−): Example 3-3) In the absence of chaotropic agent (2)
Guanidine thiocyanate (+): Example 3-1) In the presence of chaotropic agent From the foregoing, it has been revealed that the guide probe can remarkably increase the detection sensitivity for the modified nucleobase in the double-stranded target nucleic acid in the presence of the chaotropic agent.

Example 4

Measurement of Modified Nucleobase in Single-Stranded and Double-Stranded Target Nucleic Acids Using Guide Probe in the Presence of Chaotropic Agent The nucleotide sequence of the capture probe for the target nucleic acid is the nucleotide sequence of SEQ ID NO: 4 (the backbone of the nucleic acid is 2'-O-methylated RNA, the 5'-end is biotin-labeled), and the nucleotide sequence of the guide probe is the nucleotide sequence of SEQ ID NO: 5 (Guide Probe 1); those artificially synthesized by Hokkaido System Science Co., Ltd. were used. As the target nucleic acids containing 5-methylcytosine, a single-stranded target nucleic acid artificially synthesized by Hokkaido System Science Co., Ltd. and the double-stranded target nucleic acid prepared in Reference Example 1-1) were used. As the chaotropic agent, guanidine thiocyanate was used.

First, the single-stranded or double-stranded target nucleic acid containing 5-methylcytosine (10 fmol, 1 fmol, 0.1 fmol, or 0.01 fmol), the capture probe (5 pmol), and the guide probe (1 pmol) were dissolved in 100 μL of the guanidine thiocyanate (+) buffer solution (100 mM of Tris-HCl, 4.2 M of guanidine thiocyanate, and 50 mM of EDTA.2Na). The solution was subjected to a reaction [a denaturation reaction (the single-stranded target nucleic acid) or dissociation and denaturation reactions (the double-stranded target nucleic acid)] at 95° C. for 5 minutes and was subjected to a hybridization reaction at 37° C. for 1 hour to form a hybrid including the target nucleic acid, the capture probe, and the guide probe. A solution not containing the target nucleic acid was also prepared, and a similar operation was performed. To the solution after the hybridization reaction, 50 μL of the magnetic particles coated with 375 μg/mL of streptavidin (Dynabeads M-280 Streptavidin manufactured by Invitrogen) were added and were reacted at 37° C. for 30 minutes to immobilize the nucleic acid hybrid to the magnetic particles. The nucleic acid hybrid immobilized to the magnetic particles was washed with 250 μL of TBS-T three times, and 100 ng/mL of the anti-methylcytosine antibody (Clone33D3 manufactured by Nippon Gene Co., Ltd.) was added thereto by 125 μL each and was reacted at 37° C. for 1 hour. The reactant was washed with 250 μL of TBS-T three times, and 250 ng/mL of the alkaline phosphatase-labeled anti-IgG antibody (manufactured by Millipore Corporation) was added thereto by 125 μL each and was reacted at 37° C. for 30 minutes. The reactant was washed with 250 μL of TBS-T three times, and a solution of the chemiluminescent substrate AMPPD was added thereto by 110 μL each and was reacted at 37° C. for 5 minutes. Thereafter, luminescence counts were measured by the microplate reader (Arvo manufactured by PerkinElmer, Inc.).

Figure 8:
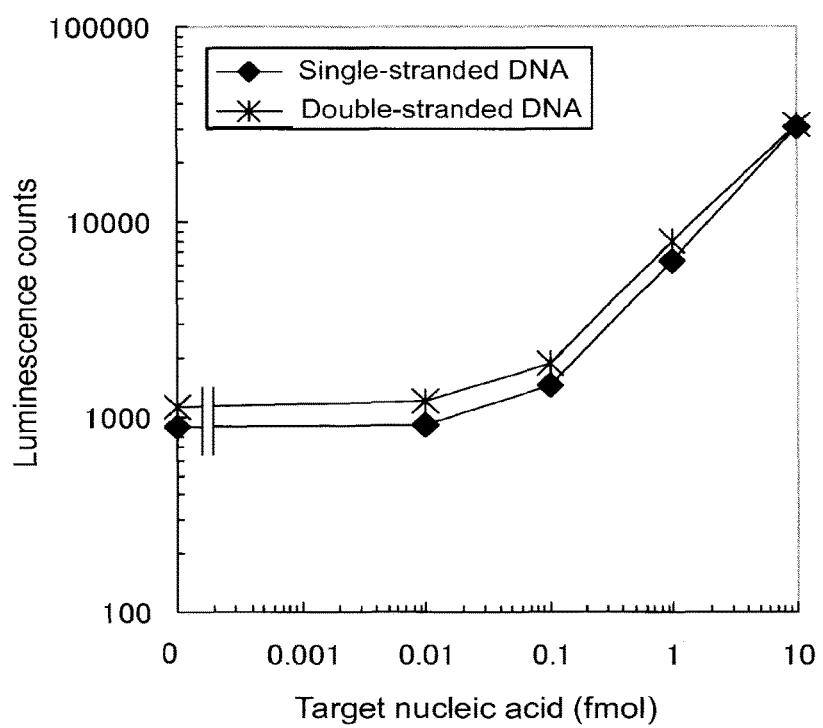
FIG. 8 is a diagram of the measurement of the modified nucleobase in the single-stranded and double-stranded target nucleic acids using the guide probe in the presence of the chaotropic agent.

As a result of the measurement, surprisingly, substantially equal luminescence counts were obtained for the single-stranded target nucleic acid and the double-stranded target nucleic acid (Table 5 and FIG. 8). This fact indicates that the guide probe can increase the detection sensitivity for the modified nucleobase in the double-stranded target nucleic acid to be substantially equal to that for the modified nucleobase in the single-stranded target nucleic acid in the presence of the chaotropic agent.

TABLE 5

Measurement of modified nucleobase in single-stranded and double-stranded target nucleic acids using guide probe in the presence of the chaotropic agent

| Buffer solution condition | Target nucleic acid | Amount of target nucleic acid | Luminescence counts | S/N |
|---|---|---|---|---|
| Guanidine thiocyanate (+) | Single-stranded DNA | 10 fmol | 30660 | 34.82 |
| | | 1 fmol | 6338 | 7.20 |
| | | 0.1 fmol | 1461 | 1.66 |
| | | 0.01 fmol | 906 | 1.03 |
| | | 0 mol | 881 | |
| | Double-stranded DNA | 10 fmol | 31156 | 27.53 |
| | | 1 fmol | 7948 | 7.02 |
| | | 0.1 fmol | 1891 | 1.67 |
| | | 0.01 fmol | 1193 | 1.05 |
| | | 0 mol | 1132 | |

From the foregoing, it has been revealed that the guide probe can measure the modified nucleobase in the target nucleic acid with high sensitivity regardless of the number of the strand of the target nucleic acid in the presence of the chaotropic agent.

Reference Example 2

Measurement of Modified Nucleobase in Single-Stranded and Double-Stranded Target Nucleic Acids Using Capture Probe and Guide Probe Tests were carried out by a method similar to that in Example 4 except that the hybridization buffer solution (5×SSC, 0.1% (v/v) Tween20) was used in place of the guanidine thiocyanate (+) buffer solution when the hybrid including the target nucleic acid, the capture probe, and the guide probe was formed.

Figure 9:
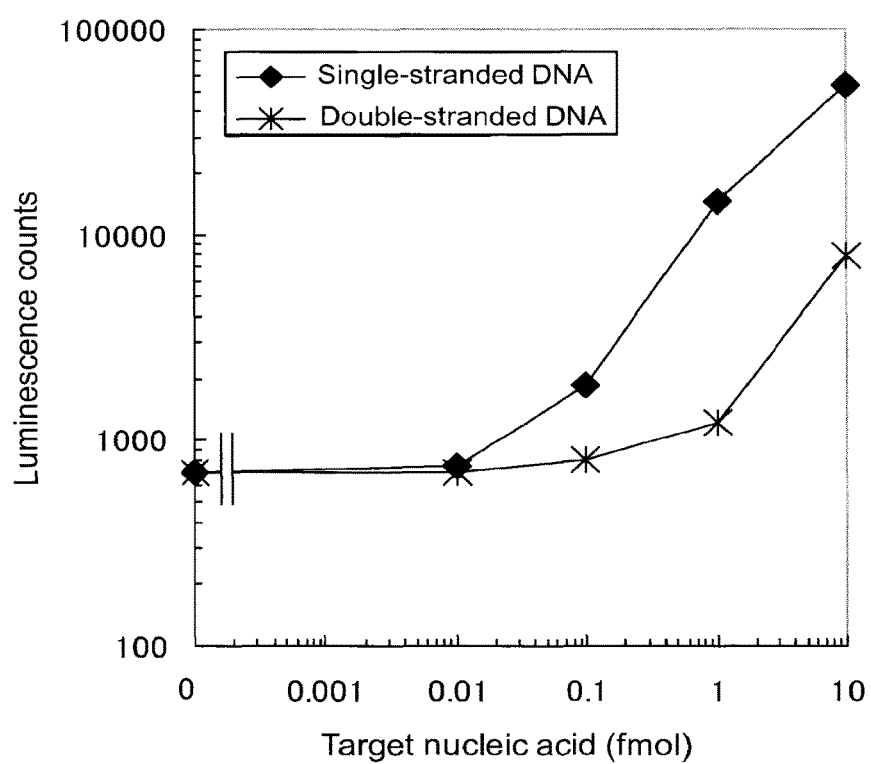
FIG. 9 is a diagram of the measurement of the modified nucleobase in the single-stranded and double-stranded target nucleic acids using the guide probe. This experiment was carried out for comparison with the experiment illustrated in FIG. 8.

As a result of the measurement, although some increase in the detection sensitivity for the modified nucleobase in the double-stranded target nucleic acid was revealed on the condition using the hybridization buffer solution (that is, use of the guide probe alone) (the difference was not as much as that revealed in Reference Example 1), the detection sensitivity for the modified nucleobase in the double-stranded target nucleic acid fell short of that for the modified nucleobase in the single-stranded target nucleic acid (Table 6 and FIG. 9). In other words, it has been proved that the guide probe can increase the detection sensitivity for the modified nucleobase in the double-stranded target nucleic acid to be substantially equal to that for the modified nucleobase in the single-stranded target nucleic acid in the presence of the chaotropic agent.

TABLE 6

Measurement of modified nucleobase in single-stranded and double-stranded target nucleic acids using guide probe

| Buffer solution condition | Target nucleic acid | Amount of target nucleic acid | Luminescence counts | S/N |
|---|---|---|---|---|
| Hybridization buffer solution | Single-stranded DNA | 10 fmol | 52777 | 75.34 |
| | | 1 fmol | 14397 | 20.55 |
| | | 0.1 fmol | 1863 | 2.66 |
| | | 0.01 fmol | 751 | 1.07 |
| | | 0 mol | 701 | |
| | Double-stranded DNA | 10 fmol | 7827 | 11.29 |
| | | 1 fmol | 1215 | 1.75 |
| | | 0.1 fmol | 789 | 1.14 |
| | | 0.01 fmol | 695 | 1.00 |
| | | 0 mol | 693 | |

Example 5

Measurement of Modified Nucleobase Using Guide Probe in the Presence of Nucleic Acid Denaturant Tests were carried out by a method similar to that in Example 3-1) except that the buffer solution (100 mM of Tris-HCl and 50 mM of EDTA.2Na) containing no nucleic acid denaturant, 4.2 M of guanidine thiocyanate, 2.7 M of imidazole, or 4 M of urea was used when the hybrid including the target nucleic acid, the capture probe, and the guide probe was formed.

Figure 10:
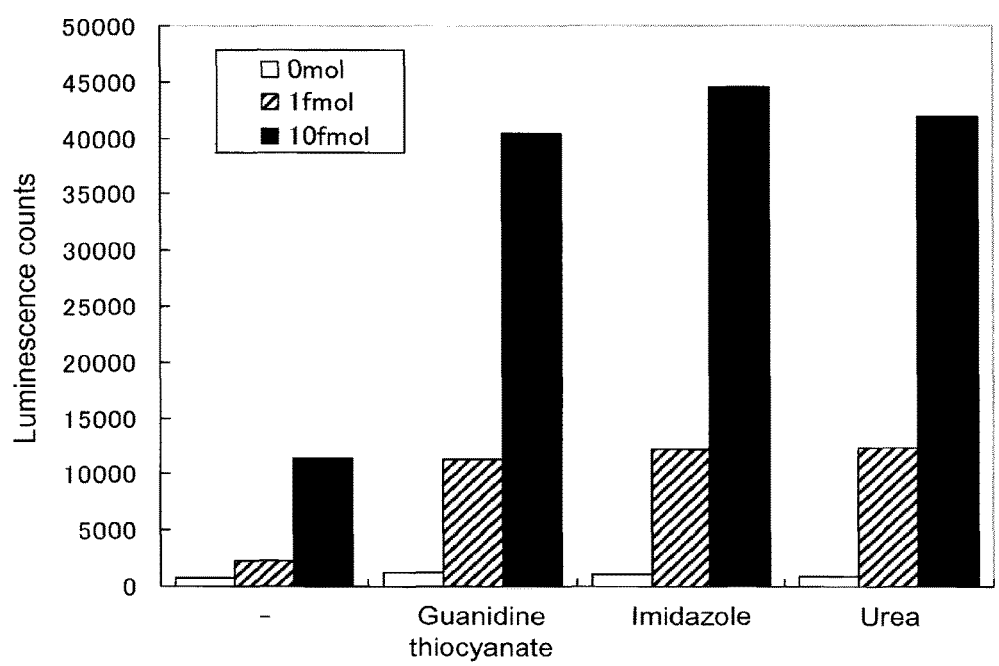
FIG. 10 is a diagram of the measurement of the modified nucleobase using the guide probe in the presence of a nucleic acid denaturant.

As a result of the measurement, the nucleic acid denaturants other than guanidine thiocyanate also produced luminescence counts equal to those of guanidine thiocyanate (Table 7 and FIG. 10). This fact indicates that the guide probe can increase the detection sensitivity for the modified nucleobase in the target nucleic acid in the presence of the nucleic acid denaturant.

TABLE 7

Measurement of modified nucleobase using guide probe in the presence of nucleic acid denaturant

| Denaturant | Amount of target nucleic acid | Luminescence counts | S/N |
|---|---|---|---|
| — | 10 fmol | 11445 | 14.0 |
| | 1 fmol | 2307 | 2.8 |
| | 0 mol | 818 | |
| Guanidine thiocyanate | 10 fmol | 40344 | 32.3 |
| | 1 fmol | 11329 | 9.1 |
| | 0 mol | 1250 | |
| Imidazole | 10 fmol | 44460 | 44.1 |
| | 1 fmol | 12171 | 12.1 |
| | 0 mol | 1009 | |
| Urea | 10 fmol | 41962 | 49.8 |
| | 1 fmol | 12298 | 14.6 |
| | 0 mol | 842 | |

—: No denaturant

From the foregoing, it has been revealed that the guide probe can measure the modified nucleobase in the target nucleic acid with high sensitivity in the presence of the nucleic acid denaturant.

Example 6

Inhibition of Formation of Secondary Structure in Site Containing Modified Nucleobase by Guide Probe The nucleotide sequence of the capture probe for the target nucleic acid is the nucleotide sequence of SEQ ID NO: 4 (the backbone of the nucleic acid is 2'-O-methylated RNA, the 5'-end is biotin-labeled), and the nucleotide sequence of the guide probe is any of the nucleotide sequences listed in Table 8; those artificially synthesized by Hokkaido System Science Co., Ltd. were used. As the target nucleic acid containing 5-methylcitosine, the double-stranded target nucleic acid prepared in Reference Example 1-1) was used.

Tests were carried out by a method similar to that in Example 3-1) except that none of the guide probes with the sequences listed in Table 8 was added or one, two, or three thereof were added by 10 pmol each.

Figure 11:
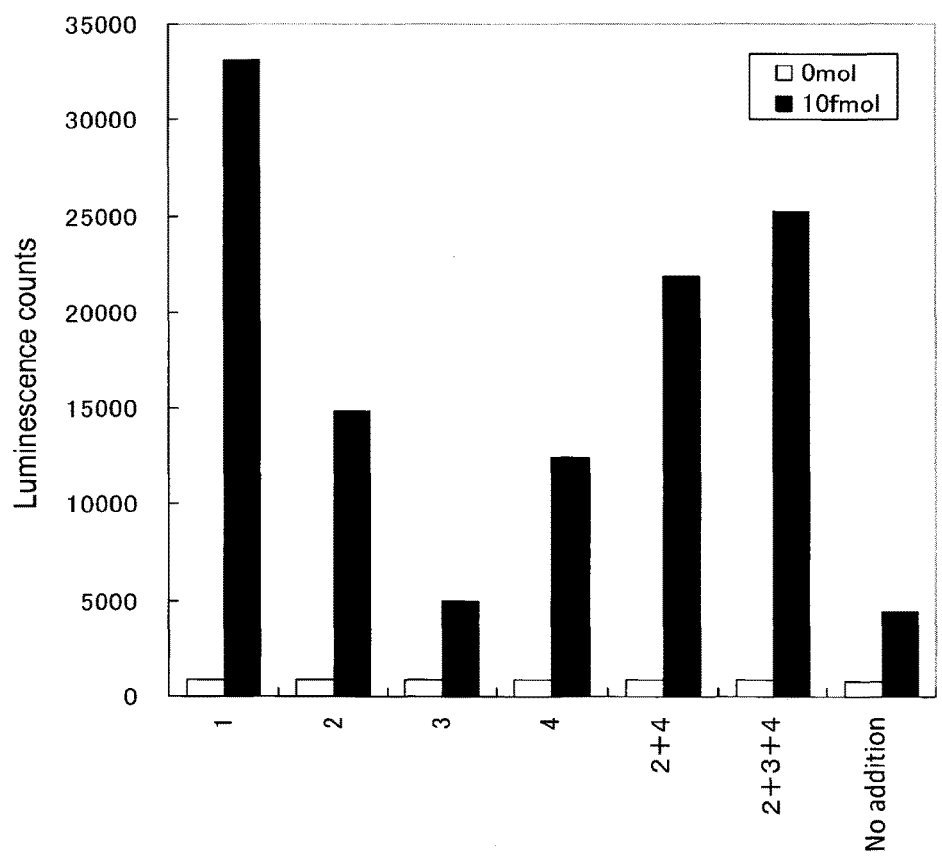
FIG. 11 is a diagram of inhibition of the formation of a secondary structure in a site containing the modified nucleobase by the guide probe. 1: Guide Probe 1; 2: Guide Probe 2; 3: Guide Probe 3; 4: Guide Probe 4; 2+4: Guide Probes 2 and 4 are added; and 2+3+4: Guide Probes 3, and 4 are added.

As a result of the measurement, although increases in the luminescence counts were revealed when the guide probes (that is, Guide Probes 1, 2, and 4) having complementarity with a site containing the modified nucleobase in the target nucleic acid were added, no increase in the luminescence counts was revealed when the guide probe (that is, Guide Probe 3) having complementarity with a site not containing the modified nucleobase in the target nucleic acid was added (Table 9 and FIG. 11). Consequently, it has been demonstrated that inhibition of the formation of the secondary structure in the site containing the modified nucleobase by the guide probe is important for increasing detection sensitivity.

TABLE 8

Nucleotide sequences of Guide Probes 1 to 4

| Guide probe | Nucleotide sequence (SEQ ID NO) |
|---|---|
| 1 | 5'-CCC AGG GAG AGC TCC CAC TCT TCC GGA GCA GGC ACC CAG ACA CTC ACC AAG TCC AAA CGT GCC ACC CAG GAC CTG CGG CTC GGA CCA AAG CTT CTA-3' (SEQ ID NO: 5) |
| 2 | 5'-TCC CAG GGA GAG CTC CCA CTC TTC CGG AGC AGG C-3' (SEQ ID NO: 6) |
| 3 | 5'-ACC CAG ACA CTC ACC AAG TC-3' (SEQ ID NO: 7) |
| 4 | 5'-CAA ACG TGC CAC CCA GGA CCT GCG GCT CGG ACC AAA GC-3' (SEQ ID NO: 8) |

TABLE 9

Inhibition of formation of secondary structure in site containing modified nucleobase by guide probe

| Guide probe | Amount of target nucleic acid | Luminescence counts | S/N |
|---|---|---|---|
| 1 | 10 fmol | 33154 | 38.2 |
|   | 0 mol | 867 |   |
| 2 | 10 fmol | 14856 | 18.2 |
|   | 0 mol | 816 |   |
| 3 | 10 fmol | 4934 | 5.5 |
|   | 0 mol | 892 |   |
| 4 | 10 fmol | 12436 | 14.2 |
|   | 0 mol | 876 |   |
| 2 + 4 | 10 fmol | 21898 | 25.1 |
|   | 0 mol | 874 |   |
| 2 + 3 + 4 | 10 fmol | 25245 | 28.8 |
|   | 0 mol | 878 |   |
| Absent | 10 fmol | 4463 | 5.5 |
|   | 0 mol | 813 |   |

2 + 4: Guide Probes 2 and 4 are added
2 + 3 + 4: Guide Probes 2, 3, and 4 are added Example 7

Investigation of Concentration of Nucleic Acid Denaturant

Tests were carried out by a method similar to that in Example 3-1) except that the concentration of guanidine thiocyanate contained in the buffer solution (100 mM of Tris-HCl, guanidine thiocyanate, and 50 mM of EDTA.2Na) for forming the hybrid of the target nucleic acid containing 5-methylcytosine (10 fmol or 1 fmol), the capture probe (5 pmol), and Guide Probe 1 (1 pmol) was set to any of the concentrations listed in Table 10. For a guanidine thiocyanate (−) buffer solution (that is, 0 M), tests were carried out similarly.

Figure 12:
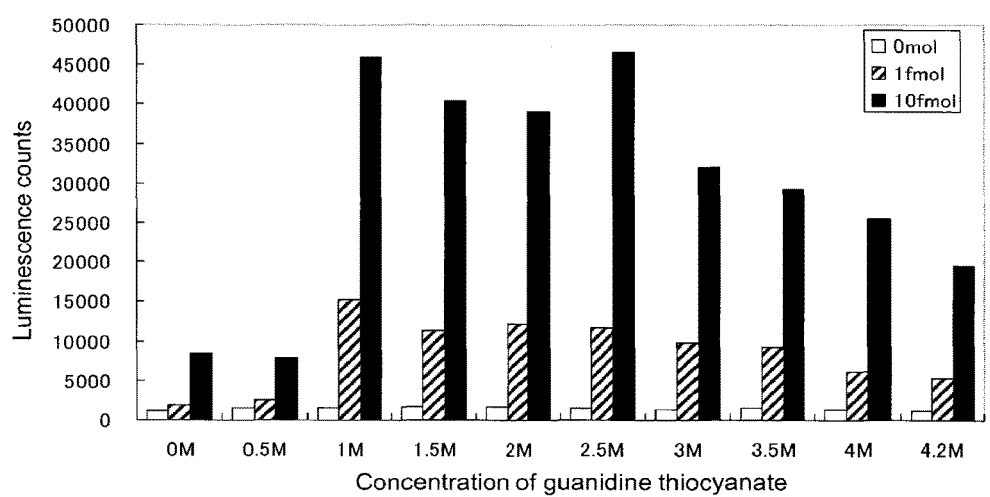
FIG. 12 is a diagram of the effect of the nucleic acid denaturant at various concentrations.

As a result of the measurement, it has been revealed that guanidine thiocyanate contained in the buffer solution in the range of 1 M to 2.5 M is the most effective (Table 10 and FIG. 12).

TABLE 10

Effect of nucleic acid denaturant at various concentrations

| Concentration of guanidine thiocyanate | Amount of target nucleic acid | Luminescence counts | S/N |
|---|---|---|---|
| 0M | 10 fmol | 8378 | 7.3 |
|   | 1 fmol | 1862 | 1.6 |
|   | 0 mol | 1140 |   |
| 0.5M | 10 fmol | 7862 | 5.4 |
|   | 1 fmol | 2599 | 1.8 |
|   | 0 mol | 1463 |   |
| 1M | 10 fmol | 45811 | 28.3 |
|   | 1 fmol | 15247 | 9.4 |
|   | 0 mol | 1621 |   |
| 1.5M | 10 fmol | 40450 | 24.0 |
|   | 1 fmol | 11275 | 6.7 |
|   | 0 mol | 1689 |   |
| 2M | 10 fmol | 39062 | 22.8 |
|   | 1 fmol | 12092 | 7.1 |
|   | 0 mol | 1713 |   |
| 2.5M | 10 fmol | 46560 | 29.7 |
|   | 1 fmol | 11571 | 7.4 |
|   | 0 mol | 1566 |   |
| 3M | 10 fmol | 32029 | 22.8 |
|   | 1 fmol | 9809 | 7.0 |
|   | 0 mol | 1404 |   |
| 3.5M | 10 fmol | 29208 | 19.8 |
|   | 1 fmol | 9316 | 6.3 |
|   | 0 mol | 1477 |   |
| 4M | 10 fmol | 25430 | 19.0 |
|   | 1 fmol | 6127 | 4.6 |
|   | 0 mol | 1340 |   |
| 4.2M | 10 fmol | 19587 | 15.6 |
|   | 1 fmol | 5322 | 4.2 |
|   | 0 mol | 1253 |   |

Example 8

Investigation of Backbone of Guide Probe

The nucleotide sequence of the capture probe for the target nucleic acid is the nucleotide sequence of SEQ ID NO: 4 (the backbone of the nucleic acid is 2'-O-methylated RNA, the 5'-end is biotin-labeled); that artificially synthesized by Hokkaido System Science Co., Ltd. was used. The nucleotide sequence of the guide probe is any of the nucleotide sequences listed in Table 11; Guide Probes 2 and 4 having DNA as the backbone of the nucleic acid were used, whereas Guide Probes 5 and 6 having 2'-O-methylated RNA or RNA as the backbone of the nucleic acid were used. Although Guide Probes 5 and 6 have the sequences equal to those of Guide Probes 2 and 4, respectively, since their backbone of the nucleic acid is 2'-O-methylated RNA or RNA, the guide probes in which the thymine base (T) was changed to the uracil base (U) were used. The guide probes artificially synthesized by Hokkaido System Science Co., Ltd. were used. As the target nucleic acid containing 5-methylcytosine, the double-stranded target nucleic acid prepared in Reference Example 1-1) was used.

Tests were carried out by a method similar to that in Example 3-1) except that none of the guide probes with the sequences listed in Table 11 was added or one or two thereof were added by 1 pmol each.

Figure 13:
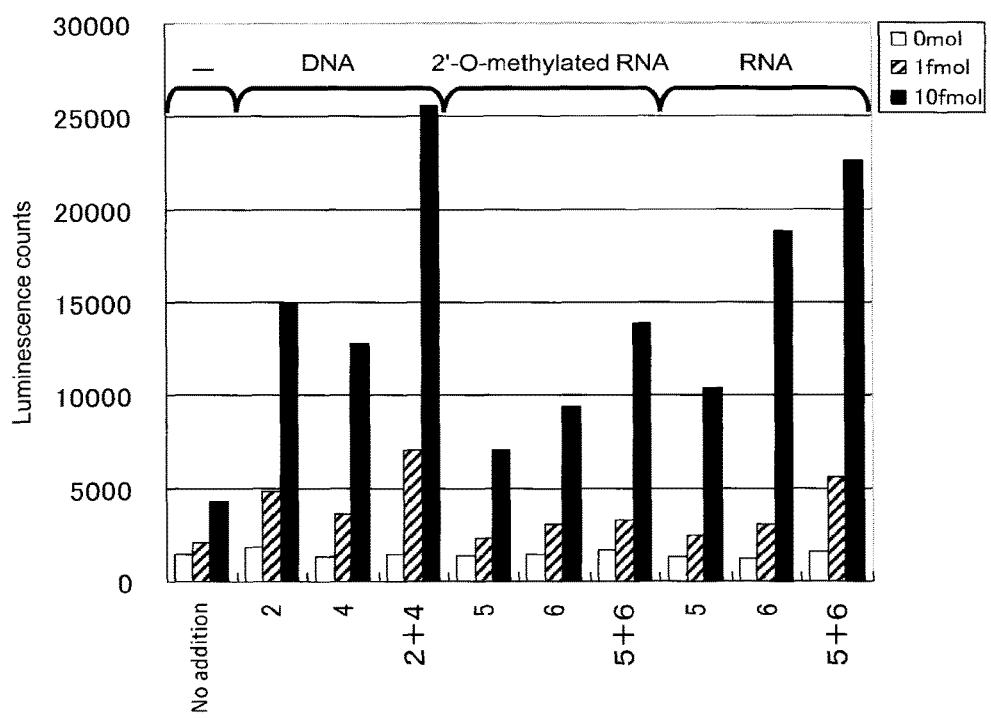
FIG. 13 is a diagram of the investigation of the backbone of the guide probe. No addition: in the absence of the guide probe; 2: Guide Probe 2; 4: Guide Probe 4; 2+4: in the presence of Guide Probes 2 and 4; 5: Guide Probe 5; 6: Guide Probe 6; 5+6: in the presence of Guide Probes 5 and 6; −: in the absence of the guide probe; DNA: the backbone of the guide probe is DNA; 2'-O-methylated RNA: the backbone of the guide probe is 2'-O-methylated RNA; and RNA: the backbone of the guide probe is RNA.

Even when the backbone of the nucleic acid used as the guide probe varied from DNA, RNA, to 2'-O-methylated RNA, increases in the luminescence counts were revealed compared with a case in which the guide probe was absent (Table 12 and FIG. 13). This fact indicates that the guide probe functions as a guide probe regardless of its backbone structure. It has also been revealed that DNA as the backbone of the guide probe is the most effective (Table 12 and FIG. 13).

TABLE 11

Nucleotide sequences of Guide Probes 2 and 4 to 6

| Guide probe | Nucleotide sequence (SEQ ID NO) |
|---|---|
| 2 | 5'-TCC AGG GAG CTC CCA CTC TTC CGG AGC AGG C-3' (SEQ ID NO: 6) |
| 4 | 5'-CAA ACG TGC CAC CCA GGA CCT GCG GCT CGG ACC AAA GC-3' (SEQ ID NO: 8) |
| 5 | 5'-UCC AGG GAG CUC CCA CUC UUC CGG AGC AGG C-3' (SEQ ID NO: 9) |
| 6 | 5'-CAA ACG UGC CAC CCA GGA CCU GCG GCU CGG ACC AAA GC-3' (SEQ ID NO: 10) |

Guide Probe 5 is given by changing T to U in sequence of Guide Probe 2
Guide Probe 6 is given by changing T to U in sequence of Guide Probe 4

TABLE 12

Investigation of backbone of guide probe

| Type of nucleic acid | Guide probe | Amount of target nucleic acid | Luminescence counts | S/N |
|---|---|---|---|---|
| DNA | 2 | 10 fmol | 14919 | 8.1 |
| | | 1 fmol | 4797 | 2.6 |
| | | 0 mol | 1843 | |
| | 4 | 10 fmol | 12771 | 9.8 |
| | | 1 fmol | 3635 | 2.8 |
| | | 0 mol | 1305 | |
| | 2 + 4 | 10 fmol | 25559 | 17.7 |
| | | 1 fmol | 7026 | 4.9 |
| | | 0 mol | 1448 | |
| 2'-O-Methylated RNA | 5 | 10 fmol | 7067 | 5.1 |
| | | 1 fmol | 2319 | 1.7 |
| | | 0 mol | 1387 | |
| | 6 | 10 fmol | 9402 | 6.6 |
| | | 1 fmol | 3085 | 2.2 |
| | | 0 mol | 1418 | |
| | 5 + 6 | 10 fmol | 13885 | 8.1 |
| | | 1 fmol | 3263 | 1.9 |
| | | 0 mol | 1720 | |

TABLE 12-continued

Investigation of backbone of guide probe

| Type of nucleic acid | Guide probe | Amount of target nucleic acid | Luminescence counts | S/N |
|---|---|---|---|---|
| RNA | 5 | 10 fmol | 10433 | 8.2 |
| | | 1 fmol | 2483 | 2.0 |
| | | 0 mol | 1269 | |
| | 6 | 10 fmol | 18815 | 15.2 |
| | | 1 fmol | 3057 | 2.5 |
| | | 0 mol | 1242 | |
| | 5 + 6 | 10 fmol | 22544 | 14.4 |
| | | 1 fmol | 5608 | 3.6 |
| | | 0 mol | 1570 | |
| Absent | | 10 fmol | 4297 | 3.0 |
| | | 1 fmol | 2096 | 1.4 |
| | | 0 mol | 1446 | |

Guide Probe 2 + 4: Guide Probes 2 and 4 are added
Guide Probe 5 + 6: Guide Probes 5 and 6 are added Example 9

Measurement of Modified Nucleobase Using Guide Probe in the Presence of Nucleic Acid Denaturant or Non-Nucleic Acid Denaturant The nucleotide sequence of the capture probe for the target nucleic acid is the nucleotide sequence of SEQ ID NO: 4 (the backbone of the nucleic acid is 2'-O-methylated RNA, the 5'-end is biotin-labeled), and the nucleotide sequence of the guide probe is the nucleotide sequence of SEQ ID NO: 5 (Guide Probe 1); those artificially synthesized by Hokkaido System Science Co., Ltd. were used. As the target nucleic acid containing 5-methylcytosine, the double-stranded target nucleic acid prepared in Reference Example 1-1) was used.

First, the target nucleic acid containing 5-methylcytosine (10 fmol or 1 fmol), the capture probe (1 pmol), and the guide probe (1 pmol) were dissolved in 100 µL of the buffer solution (100 mM of Tris-HCl and 50 mM of EDTA.2Na). In the buffer solution, a similar solution was prepared using a buffer solution containing 1.5 M of guanidine thiocyanate, 1.5 M of imidazole, 1.5 M of pyrazole, 1.5 M of urea, 1% (v/v) of Tween20, or 1% (v/v) of sodium lauryl sulfate. The solution was subjected to dissociation and denaturation reactions at 95° C. for 5 minutes and was subjected to a hybridization reaction at 37° C. for 1 hour to form a hybrid including the target nucleic acid, the capture probe, and the guide probe. A solution not containing the target nucleic acid was also prepared, and a similar operation was performed. To the solution after the hybridization reaction, 50 µL of the magnetic particles coated with 375 µg/mL of streptavidin (Dynabeads M-280 Streptavidin manufactured by Invitrogen) were added and were reacted at 37° C. for 30 minutes to immobilize the nucleic acid hybrid to the magnetic particles. The nucleic acid hybrid immobilized to the magnetic particles was washed with 250 µL of TBS-T three times, and 100 ng/mL of the anti-methylcytosine antibody (Clone33D3 manufactured by Nippon Gene Co., Ltd.) was added thereto by 125 µL each and was reacted at 37° C. for 1 hour. The reactant was washed with 250 µL of TBS-T three times, and 250 ng/mL of the alkaline phosphatase-labeled anti-IgG antibody (manufactured by Millipore Corporation) was added thereto by 125 µL each and was reacted at 37° C. for 30 minutes. The reactant was washed with 250 µL of TBS-T three times, and a solution of the chemiluminescent substrate AMPPD was added thereto by 110 μL each and was reacted at 37° C. for 5 minutes. Thereafter, luminescence counts were measured by the microplate reader (Arvo manufactured by PerkinElmer, Inc.).

Figure 14:
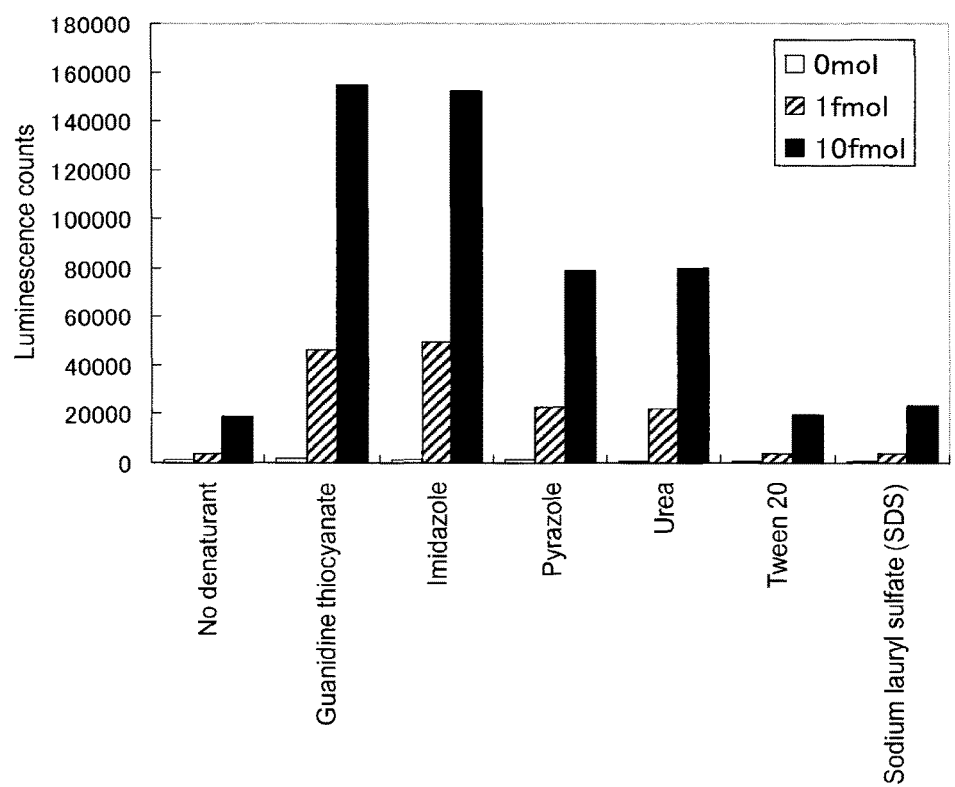
FIG. 14 is a diagram of the measurement of the modified nucleobase using the guide probe in the presence of the nucleic acid denaturant (the chaotropic agent and an electron donating compound) or a non-nucleic acid denaturant (a surfactant).

As a result of the measurement, the surfactants (Tween20 and SDS) as non-nucleic acid denaturants did not increase the luminescence counts significantly compared with the condition of no denaturant (−) (Table 13 and FIG. 14). The chaotropic agents (guanidine thiocyanate and urea) and the electron donating compounds (imidazole and pyrazole) as the nucleic acid denaturants increased the luminescence counts significantly compared with the condition of no denaturant (−) (Table 13 and FIG. 14).

TABLE 13

Measurement of modified nucleobase in target nucleic acid using guide probe in the presence of nucleic acid denaturant or non-nucleic acid denaturant

| Denaturant | Amount of target nucleic acid | Luminescence counts | S/N |
|---|---|---|---|
| — | 10 fmol | 18869 | 19.3 |
|   | 1 fmol | 4088 | 4.2 |
|   | 0 mol | 977 |   |
| Guanidine thiocyanate | 10 fmol | 154679 | 73.6 |
|   | 1 fmol | 46165 | 22.0 |
|   | 0 mol | 2102 |   |
| Imidazole | 10 fmol | 151900 | 145.1 |
|   | 1 fmol | 49139 | 46.9 |
|   | 0 mol | 1047 |   |
| Pyrazole | 10 fmol | 78880 | 77.0 |
|   | 1 fmol | 22857 | 22.3 |
|   | 0 mol | 1024 |   |
| Urea | 10 fmol | 80014 | 93.4 |
|   | 1 fmol | 22447 | 26.2 |
|   | 0 mol | 857 |   |
| Tween 20 | 10 fmol | 19919 | 24.4 |
|   | 1 fmol | 3499 | 4.3 |
|   | 0 mol | 816 |   |
| Sodium lauryl sulfate (SDS) | 10 fmol | 23520 | 25.8 |
|   | 1 fmol | 3612 | 4.0 |
|   | 0 mol | 913 |   |

—: No denaturant

From the foregoing, it has been revealed that the effect of the guide probe can be enhanced by the nucleic acid denaturant but cannot be enhanced by the non-nucleic acid denaturant.

Example 10

Measurement of Modified Nucleobase Using Guide Probe in the Presence of Both Nucleic Acid Denaturant and Surfactant Tests were carried out by a method similar to that in Example 9 except that the buffer solution (100 mM of Tris-HCl and 50 mM of EDTA.2Na) not containing the nucleic acid denaturant, 1.5 M of a guanidine thiocyanate (+) buffer solution (100 mM of Tris-HCl and 50 mM of EDTA.2Na), the buffer solution (100 mM of Tris-HCl and 50 mM of EDTA.2Na) containing 1.5 M of guanidine thiocyanate and 1% (v/v) of Tween20, or the buffer solution (100 mM of Tris-HCl and 50 mM of EDTA.2Na) containing 1.5 M of guanidine thiocyanate and 1% (v/v) of Tween80 was used when the hybrid including the target nucleic acid, the capture probe, and the guide probe was formed.

Figure 15:
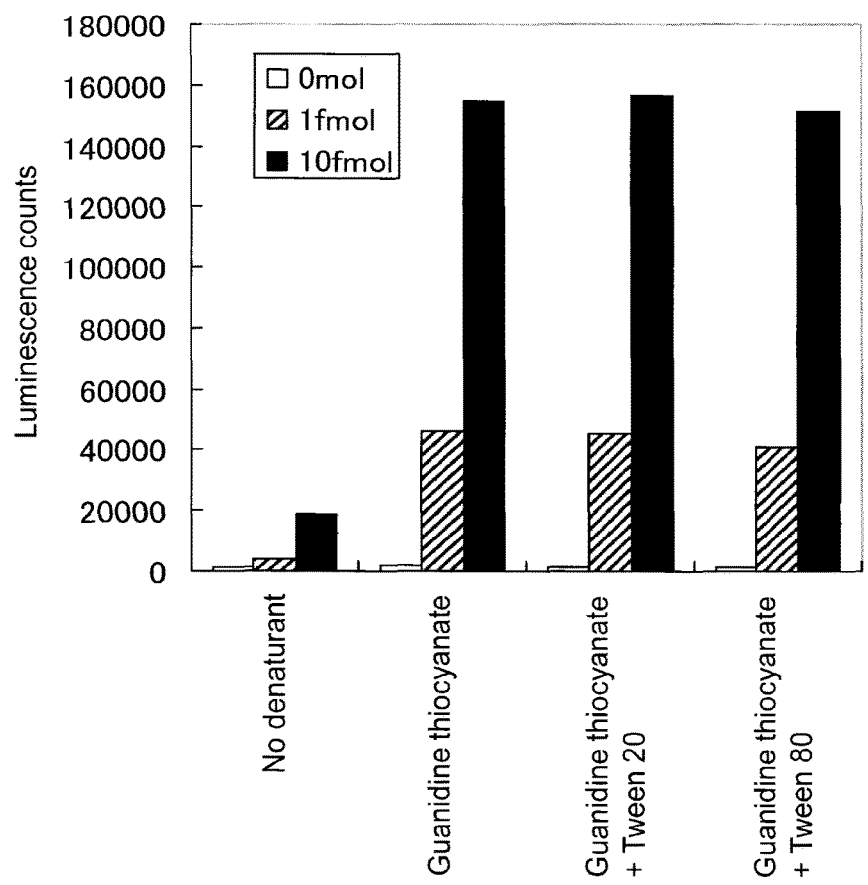
FIG. 15 is a diagram of the measurement (luminescence counts) of the modified nucleobase in the target nucleic acid using the guide probe in the presence of both the nucleic acid denaturant and the surfactant.
Figure 16:
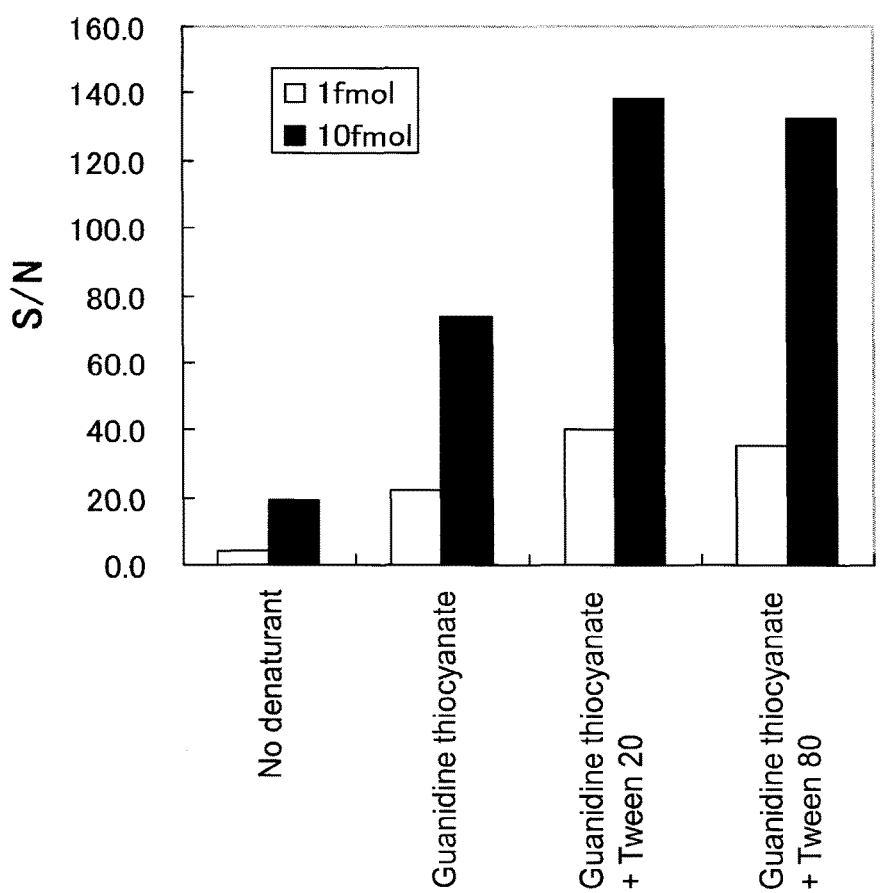
FIG. 16 is a diagram of the measurement (S/N) of the modified nucleobase in the target nucleic acid using the guide probe in the presence of both the nucleic acid denaturant and the surfactant. Signal-to-noise ratio (S/N): luminescence counts of an amount of the target nucleic acid (fmol)/luminescence counts in the absence (that is, 0 mol) of the target nucleic acid.

As a result of the measurement, the buffer solution containing the nucleic acid denaturant and the surfactant caused a decrease in the luminescence counts (the background value) and an increase in S/N compared with the buffer solution containing the nucleic acid denaturant alone (Table 14 and FIGS. 15 and 16). In other words, in the method of the present invention using the guide probe and the nucleic acid denaturant, it is considered that the surfactant has an effect of canceling an increase in the background value caused by the nucleic acid denaturant.

TABLE 14

Measurement of modified nucleobase using guide probe in the presence of both nucleic acid denaturant and surfactant

| Nucleic acid denaturant ± Surfactant | Amount of target nucleic acid | Luminescence counts | S/N |
|---|---|---|---|
| — | 10 fmol | 18869 | 19.3 |
|   | 1 fmol | 4088 | 4.2 |
|   | 0 mol | 977 |   |
| Guanidine thiocyanate | 10 fmol | 154679 | 73.6 |
|   | 1 fmol | 46165 | 22.0 |
|   | 0 mol | 2102 |   |
| Guanidine thiocyanate + Tween20 | 10 fmol | 156474 | 138.7 |
|   | 1 fmol | 45393 | 40.2 |
|   | 0 mol | 1128 |   |
| Guanidine thiocyanate + Tween80 | 10 fmol | 151366 | 132.4 |
|   | 1 fmol | 40724 | 35.6 |
|   | 0 mol | 1143 |   |

—: No denaturant

From the foregoing, it has been revealed that the guide probe can measure the modified nucleobase in the target nucleic acid with high sensitivity in the presence of both the nucleic acid denaturant and the surfactant.

(Details of Guide Probes)

For reference, Table 15 lists details of the guide probes used in the experiments.

TABLE 15

Details of guide probes used in experiments

| Guide probe | Hybridized region in target nucleic acid (SEQ ID NO: 3) (positions from 5' end) | Number of bulge structures (number of unpaired methylated cytosines) | Distance from capture probe in hybrid |
|---|---|---|---|
| 1 | Positions at 1 to 110 | 14 | 3 nucleotide residues |
| 2 | Positions at 75 to 111 | 4 | 2 nucleotide residues |
| 3 (or 5) | Positions at 54 to 73 | 0 | 40 nucleotide residues |
| 4 (or 6) | Positions at 7 to 52 | 8 | 61 nucleotide residues |

INDUSTRIAL APPLICABILITY

The method and kit of the present invention are useful for measuring a modified nucleobase.

The invention claimed is:

1. A method for measuring a modified nucleobase, the method comprising:
   (1) reacting a nucleic acid sample comprising a target nucleic acid containing the modified nucleobase, a capture probe, and a guide probe in a solution by incubation to form a hybrid including the target nucleic acid, the capture probe, and the guide probe;
   (2) measuring the modified nucleobase using an antibody against the modified nucleobase in the solution comprising the hybrid obtained at (1),
   wherein the capture probe is a nucleic acid molecule having the capability of hybridizing with the target nucleic acid,
   wherein the guide probe hybridizes with the target nucleic acid in a second region different from a first region in the target nucleic acid with which the capture probe hybridizes,
   wherein the guide probe is designed so as not to hybridize with the capture probe, wherein the capture probe and the guide probe are not bound to the antibody.

2. The method according to claim 1, further comprising combining the nucleic acid sample with the capture probe and the guide probe in a solution to prepare a solution comprising the nucleic acid sample, the capture probe, and the guide probe.

3. The method according to claim 1, wherein the nucleic acid sample is a sample comprising a single-stranded target nucleic acid containing the modified nucleobase.

4. The method according to claim 1, wherein the nucleic acid sample is a sample comprising a double-stranded target nucleic acid containing the modified nucleobase.

5. The method according to claim 1, wherein the nucleic acid sample is a sample comprising a target DNA containing the modified nucleobase.

6. The method according to claim 1, comprising incubating the nucleic acid sample, the capture probe, and the guide probe in a solution in the presence of a nucleic acid denaturant.

7. The method according to claim 1, comprising incubating the nucleic acid sample, the capture probe, and the guide probe in a solution in the presence of both the nucleic acid denaturant and a surfactant.

8. The method according to claim 1, wherein the capture probe is a nucleic acid probe heterogeneous to the target nucleic acid.

9. The method according to claim 1, wherein the guide probe is a nucleic acid probe homogeneous to the target nucleic acid.

10. The method according to claim 1, wherein a nucleobase composing the modified nucleobase is cytosine.

11. The method according to claim 1, wherein the modified nucleobase is methylcytosine.

\* \* \* \* \*

SEQUENCE LISTING

<160> NUMBER OF SEQ ID NOS: 10

<210> SEQ ID NO 1
<211> LENGTH: 21
<212> TYPE: DNA
<213> ORGANISM: Artificial Sequence
<220> FEATURE:
<223> OTHER INFORMATION: Forward primer for amplifying a target nucleic
      acid

<400> SEQUENCE: 1
tagaacgctt tgcgtcccga c                                          21

<210> SEQ ID NO 2
<211> LENGTH: 21
<212> TYPE: DNA
<213> ORGANISM: Artificial Sequence
<220> FEATURE:
<223> OTHER INFORMATION: Reverse primer for amplifying a target nucleic
      acid

<400> SEQUENCE: 2
ctgcaggacc actcgaggct g                                          21

<210> SEQ ID NO 3
<211> LENGTH: 138
<212> TYPE: DNA
<213> ORGANISM: Artificial Sequence
<220> FEATURE:
<223> OTHER INFORMATION: One example of target nucleic acids to be
      detected in the present invention

<400> SEQUENCE: 3
tagaacgctt tgcgtcccga cgcccgcagg tcctcgcggt gcgcaccgtt tgcgacttgg    60
tgagtgtctg ggtcgcctcg ctcccggaag agtgcggagc tctccctcgg gacggtggca   120
gcctcgagtg gtcctgca                                                138

<210> SEQ ID NO 4
<211> LENGTH: 24
<212> TYPE: RNA
<213> ORGANISM: Artificial Sequence
<220> FEATURE:
<223> OTHER INFORMATION: One example of capturing probes to be used in
      the present invention.  The nucleotides that constitute this
      capturing probe are 2'-O-methylated

<400> SEQUENCE: 4
ugcaggacca cucgaggcug ccac                                       24

<210> SEQ ID NO 5
<211> LENGTH: 96
<212> TYPE: DNA
<213> ORGANISM: Artificial Sequence
<220> FEATURE:
<223> OTHER INFORMATION: Guide probe 1

<400> SEQUENCE: 5
cccagggaga gctcccactc ttccggagca ggcacccaga cactcaccaa gtccaaacgt    60
gccacccagg acctgcggct cggaccaaag cttcta                             96

<210> SEQ ID NO 6
<211> LENGTH: 34
<212> TYPE: DNA
<213> ORGANISM: Artificial Sequence
<220> FEATURE:

```
<223> OTHER INFORMATION: Guide probe 2

<400> SEQUENCE: 6
tcccagggag agctcccact cttccggagc aggc                                    34

<210> SEQ ID NO 7
<211> LENGTH: 20
<212> TYPE: DNA
<213> ORGANISM: Artificial Sequence
<220> FEATURE:
<223> OTHER INFORMATION: Guide probe 3

<400> SEQUENCE: 7
acccagacac tcaccaagtc                                                    20

<210> SEQ ID NO 8
<211> LENGTH: 38
<212> TYPE: DNA
<213> ORGANISM: Artificial Sequence
<220> FEATURE:
<223> OTHER INFORMATION: Guide probe 4

<400> SEQUENCE: 8
caaacgtgcc acccaggacc tgcggctcgg accaaagc                                38

<210> SEQ ID NO 9
<211> LENGTH: 34
<212> TYPE: RNA
<213> ORGANISM: Artificial Sequence
<220> FEATURE:
<223> OTHER INFORMATION: Guide probe 5

<400> SEQUENCE: 9
ucccagggag agcucccacu cuuccggagc aggc                                    34

<210> SEQ ID NO 10
<211> LENGTH: 38
<212> TYPE: RNA
<213> ORGANISM: Artificial Sequence
<220> FEATURE:
<223> OTHER INFORMATION: Guide probe 6

<400> SEQUENCE: 10
caaacgugcc acccaggacc ugcggcucgg accaaagc                                38
```